(12) United States Patent
Williams et al.

(10) Patent No.: US 7,604,931 B2
(45) Date of Patent: Oct. 20, 2009

(54) CRIPTO MUTANT AND USES THEREOF

(75) Inventors: Kevin P. Williams, Natick, MA (US); Susan Foley, Milford, MA (US); Susan Schiffer, Lexington, MA (US); Bruno Domon, Rockville, MD (US); Michele Sanicola-Nadel, Winchester, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 627 days.

(21) Appl. No.: 10/390,566

(22) Filed: Mar. 17, 2003

(65) Prior Publication Data

US 2003/0232755 A1 Dec. 18, 2003

Related U.S. Application Data

(63) Continuation of application No. PCT/US01/29066, filed on Sep. 18, 2001.

(60) Provisional application No. 60/233,148, filed on Sep. 18, 2000.

(51) Int. Cl.
*C12Q 1/00* (2006.01)
*A61K 38/00* (2006.01)

(52) U.S. Cl. ............................................. 435/4; 514/2
(58) Field of Classification Search ................. 530/350; 514/2; 435/7.1
See application file for complete search history.

(56) References Cited

U.S. PATENT DOCUMENTS 5,654,140 A 8/1997 Persico et al.
5,854,399 A 12/1998 Salomon et al.

FOREIGN PATENT DOCUMENTS

WO WO-96/39420 A1 12/1996
WO WO-98/33924 A1 8/1998
WO WO-00/06723 A1 2/2000

OTHER PUBLICATIONS

Bowie et al (Science, 1990, 247:1306-1310).*
Gura (Science, 1997, 278:1041-1042).*
Jain (Sci. Am., 1994, 271:58-65).*
Curti (Crit. Rev. in Oncology/Hematology, 1993, 14:29-39).*
Schiffer et al, J of Biological Chemistry, 2001, 276:27769-37778.*
Adkins et al, J of Clinical Investigation, 2003, 112:575-587.*
Yan et al, 2002, Molecular and Cellular Biology, 4439-4449.*
Schiffer et al, 2001, J Biol Chem, 276:37769-37778.*
Liguori et al (Mammalian Genome, 1996, 7:344-348).*
Shen (J of Clinical Investigation, 2003, 112:500-502).*
Bianco et al (Cancer Research, 2003, 63:1192-1197).*
Zips et al. (2005, In Vivo, 19:1-7).*
Bianco et al, 2002, Mol Cell Biol, 22:2586-2597.*
Adkins et al, 2003, J Clin Invest, 112:575-587.*
Yeo et al, 2001, Molecular Cell, 7:949-957.*
Ciardiello, F., et al., "Inhibition of CRIPTO expression and tumorigenicity in human colon cancer cells by antisense RNA and oligodeoxynucleotides," *Proceedings of the American Association for Cancer Research.*, vol. 35:562 (1994).
Ciardiello, Fortunato, et al., "Inhibition of CRIPTO expression and tumorigenicity in human colon cells by antisense RNA and oligodeoxynucleotides," *Oncogene*, vol. 9:291-298 (1994).
Harris, Reed J., et al., "O-Linked fucose and other post-translational modifications unique to EGF modules," *Glycobiology*, vol. 3(3):219-224 (1993).
Lohmeyer, Matthias, et al., "Chemical Synthesis, Structural Modeling, and Biological Activity of the Epidermal Growth Factor-Like Domain of Human *Cripto*," *Biochemistry*, vol. 36(13):3837-3845 (1997).
Rabbani, Shafaat A., et al., "Structural Requirements for the Growth Factor Activity of the Amino-terminal Domain of Urokinase," *The Journal of Biological Chemistry*, vol. 267(20):14151-14156 (1992).
Schiffer, Susan G., et al., "Fucosylation of Cripto Is Required for Its Ability to Facilitate Nodal Signaling," *The Journal of Biological Chemistry*, vol. 276(41):37769-37778 (2001).
International Search Report to PCT/US01/29066 (Nov. 9, 2002), 8 pages.

* cited by examiner

*Primary Examiner*—Laura B Goddard
(74) *Attorney, Agent, or Firm*—Lahive & Cockfield, LLP; Megan E. Williams

(57) ABSTRACT

The present invention is based on the discovery that CRIPTO mutants each comprising at least one amino acid substitution from a CRIPTO polypeptide demonstrate tumor blocking activity.

7 Claims, 6 Drawing Sheets

Figure 2:
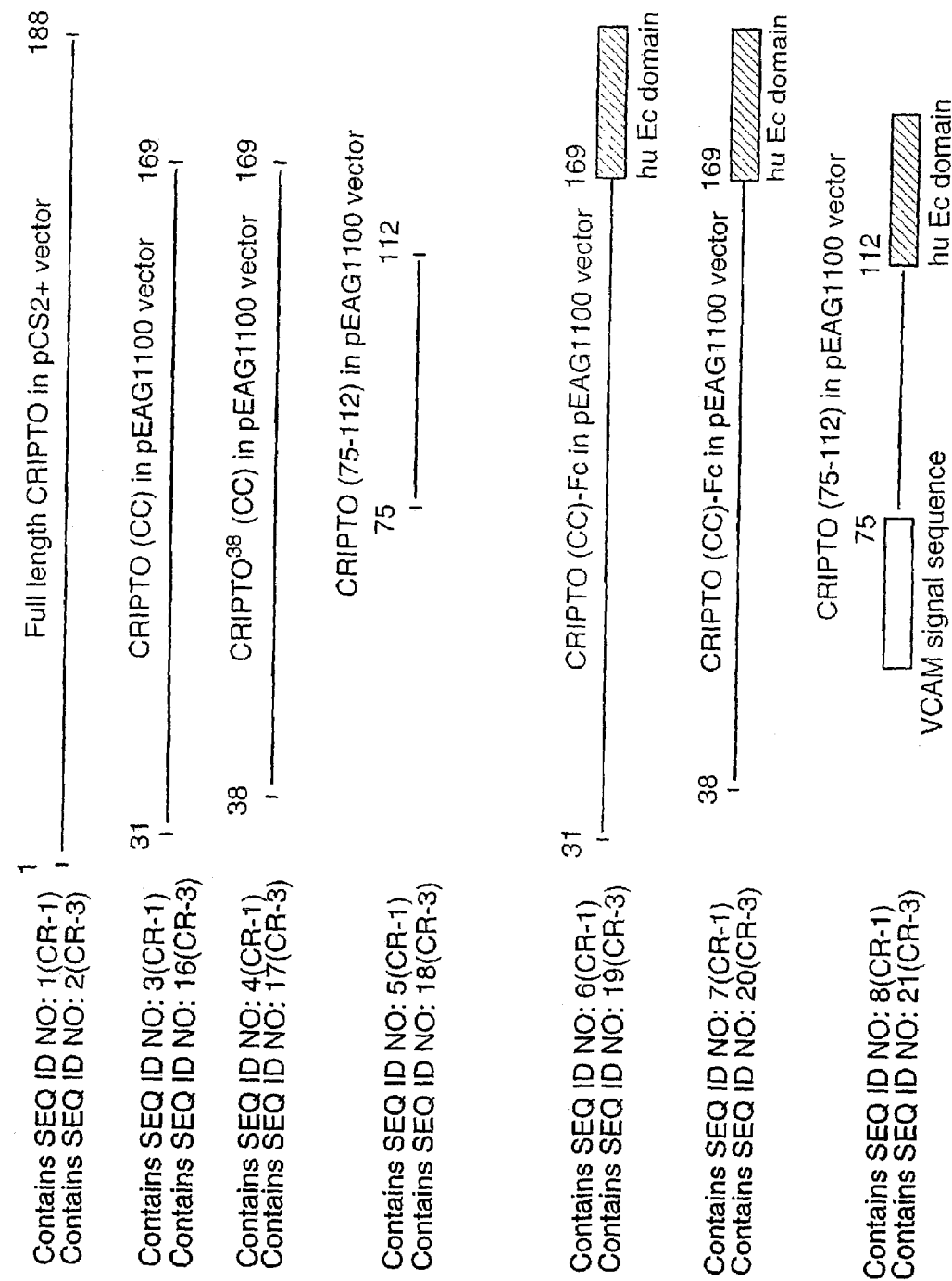

Alignment of human Cripto-1 and human Cripto-3

```
CR-1  M¹DCRKMARFSYSVIWIMAISKVFELGLVAGLGHQEFARPSRGYLAFRDDS
CR-3  M¹DCRKMVRFSYSVIWIMAISKAFELGLVAGLGHQEFARPSRGDLAFRDDS

CR-1  IWPQEEPAIRPRSSQRVPPMGIQHSKELNRTCCLNGGTCMLGSFCACPPS
CR-3  IWPQEEPAIRPRSSQRVLPMGIQHSKELNRTCCLNGGTCMLESFCACPPS

CR-1  FYGRNCEHDVRKENCGSVPHDTWLPKKCSLCKCWHGQLRCFPQAFLPGCD
Cr-3  FYGRNCEHDVRKENCGSVPHDTWLPKKCSLCKCWHGQLRCFPQAFLPGCD

CR-1  GLVMDEHLVASRTPELPPSARTTTFMLVGICLSIQSYY¹⁸⁸
CR-3  GLVMDEHLVASRTPELPPSARTTTFMLAGICLSIQSYY¹⁸⁸
```

FIG. 1

Electrospray mass spectrum of deglycosylated and reduced Cripto-1(cC)-Fc

Assignments:

| Peak | Measured Mass (Da) | CR(CC)-Fc residues (+ predicted modification) |
|---|---|---|
| A: | 41116 | 31-396; |
| B: | 41262 | 31-396 + Fuc; |
| C: | 41391 | 31-397 + Fuc; |
| D: | 41773 | 31-396 + HexNAcHexNeuAc; |
| E: | 41919 | 31-396 + Fuc + HexNAcHexNeuAc; |
| F: | 42052 | 31-397 + Fuc + HexNAcHexNeuAc; |
| G: | 42210 | 31-396 + Fuc + HexNAcHexNeuAc$_2$; |
| H: | 42575 | 31-396 + Fuc + HexNAc$_2$Hex$_2$NeuAc$_2$; |
| I: | 42870 | 31-396 + Fuc + HexNAc$_2$Hex$_2$NeuAc$_3$ |

…

CRIPTO MUTANT AND USES THEREOF

This application is a continuation of PCT/US01/29066 filed Sep. 18, 2001 which claims benefit of application Ser. No. 60/233,148 filed Sep. 18, 2000.

FIELD OF THE INVENTION

The invention relates generally to CRIPTO mutant and uses thereof.

BACKGROUND OF THE INVENTION

CRIPTO-1 (CR-1, human; Cr-1, mouse) also known as teratocarcinoma-derived growth factor-1 (U.S. Pat. Nos. 5,792,616; 5,256,643; 5,654,140), and CRIPTO-3 (CR-3, human; Cr-3, mouse) (U.S. Pat. Nos. 5,264,557; 5,620,866; 5,650,285), collectively referred to herein as CRIPTO, are EGF-related proteins. Their genes are expressed in the developing embryo, in normal adult tissues and in tumor cells, including but not limited to, breast cancer cells and colon cancer cells.

It is a discovery of the present invention that CRIPTO expressed in mammalian cells is modified with O-linked fucose, an unusual form of O-linked glycosylation, at amino acid residue threonine-88 of CRIPTO polypeptide as depicted in FIG. 1. Enzymes that add fucose modifications to proteins, recognize a seven amino acid configuration ("fucosylation site"). It is a discovery of the present invention that two residues in particular at positions N−1 (i.e. glycine residue 86 from CRIPTO polypeptides shown in FIG. 1) and N−2 (glycine residue 87 from CRIPTO polypeptides shown in FIG. 1) are required for fucosylation of threonine-88 to occur. Morever, it is a discovery of the present invention that non-fucosylated forms of CRIPTO which act as functional antagonists have anti-tumor activity. Non-fucosylated forms of CRIPTO that can act as functional antagonists include but are not limited to mutant CRIPTO polypeptides which alter the binding of CRIPTO to a CRIPTO binding partner. There is no evidence for the O-linked fucose modification in any of the soluble EGF-ligands, i.e. epidermal growth factor, transforming growth factor alpha, heregulin.

From a diagnostic or therapeutic perspective, there is considerable interest for the development of CRIPTO mutants with desirable anti-carcinogenic properties.

SUMMARY OF THE INVENTION

The present invention relates to CRIPTO mutant, including CRIPTO variants and fragments thereof, preferably CRIPTO mutants having at least one amino acid substitution at a fucosylation site of a CRIPTO polypeptide wherein the amino acid is substituted with another amino acid which is different form that present in the CRIPTO polypeptide.

In one embodiment at least one amino acid from a CRIPTO polypeptide or functional fragment thereof is substituted with another amino acid which is different from that present in the CRIPTO polypeptide, wherein the amino acid substitution is selected from the group consisting of amino acid residues 86, 87, and 88 of the amino acid sequence of the CRIPTO polypeptide.

In one embodiment the CRIPTO polypeptide is selected from the group consisting of the polypeptide shown in SEQ ID NO: 1 (full length CR-1) or SEQ ID NO: 2 (full length CR-3) or functional fragment thereof; the polypeptide shown in SEQ ID NO: 1 (full length CR-1) or SEQ ID NO: 2 (full length CR-3) or functional fragment thereof, lacking its associated signal peptide; or the domain of the polypeptide shown in SEQ ID NO: 5 [aa75-aa112 CR-1], SEQ ID NO: 18 [aa75-aa112 CR-3], SEQ ID NO: 4 [38aa-169aa CR-1], SEQ ID NO: 17 [38aa-169aa CR-3], SEQ ID NO:3 [31aa-169aa CR-1] or SEQ ID NO: 16 [31aa-169aa CR-3] or functional fragment thereof. In a preferred embodiment the one or more substitutions are amino acids selected from the group consisting of an alanine or a glycine.

In another embodiment the CRIPTO mutant comprises a defucosylation modification at position 88 of a CRIPTO polypeptide. The CRIPTO polypeptides being selected from the group consisting of the polypeptide shown in SEQ ID NO: 1 (full length CR-1) or SEQ ID NO: 2 (full length CR-3) or functional fragment thereof; the polypeptide shown in SEQ ID NO: 1 (full length CR-1) or SEQ ID NO: 2 (full length CR-3), lacking its associated signal peptide or functional fragment thereof; or the domain of the polypeptide shown in SEQ ID NO: 5 [aa75-aa112 CR-1], SEQ ID NO: 18 [aa75-aa112 CR-3], SEQ ID NO: 4 [38aa-169aa CR-1], SEQ ID NO: 17 [38aa-169aa CR-3], SEQ ID NO:3 [31aa-169aa CR-1] or SEQ ID NO: 16 [31aa-169aa CR-3] or functional fragment thereof.

Also provided are nucleic acid sequences encoding the aforementioned CRIPTO mutants and functional fragments thereof. In one embodiment the invention includes an isolated nucleic acid encoding a sequence that hybridizes under stringent conditions to a hybridization probe, the nucleotide sequence of the probe consisting of the coding sequence of SEQ ID NO: 36 (CR-1) or SEQ ID NO: 37 (CR-3) or the complement of the coding sequence of SEQ ID NO: 36 (CR-1) or SEQ ID NO: 37 (CR-3) and further comprising at least one amino substitution, wherein the amino acid substitution is selected from the group consisting of amino acid residues 86, 87, and 88 of the amino acid sequence of the CRIPTO polypeptide.

In another embodiment, the present invention provides chimeric molecules comprising an mutant CRIPTO polypeptide according to the aforementioned CRIPTO mutants and functional fragments thereof and further comprising a heterologous polypeptide. In one embodiment the heterologous polypeptide is fused to the C-terminal of the mutant CRIPTO polypeptide. In an alternative embodiment, the heterologous polypeptide is fused to the N-terminal of the mutant CRIPTO polypeptide. The heterologous polypeptides include but are not limited to glutathione-S-transferase, DNA binding domains, polymerase activating domains, histidine tags, HSA tags, epitope tag sequence and Fc regions of immunoglobulins.

In another embodiment the invention provides chimeric molecule comprising an mutant CRIPTO polypeptide according to the aforementioned CRIPTO mutants and further comprising a synthetic polymer. A non-limiting example of a synthetic polymer includes PEG (polyethylene glycol).

In another embodiment, the present invention provides methods for inhibiting the growth of a tumor cell comprising exposing the tumor cell to an effective amount of the aforementioned modified polypeptides. In a particular embodiment, the tumor cell is exposed in vivo. In another particular embodiment, the tumor cell is exposed in vitro.

In another embodiment, the present invention provides a method for treating or reducing the advancement, severity or effects of a disease associated with undesired cell proliferation, comprising administering to the subject an effective amount of the aforementioned polypeptides. In a specific embodiment, the disease or condition is associated with undesired cell proliferation. In second specific embodiment the disease or condition is associated with undesired cell proliferation is a cancer. In a third specific embodiment, the cancer is selected from the group consisting of breast cancer, ovarian cancer, renal cancer, colorectal cancer, uterine cancer, prostate cancer, lung cancer, bladder cancer, central nervous system cancer, melanoma or leukemia.

The foregoing and other objects, features, aspects and advantages of the present invention, as well as the invention itself, will be more fully understood from the following description of preferred embodiments.

DRAWINGS

FIG. 1. Alignment of human Cripto-1 and human Cripto-3 proteins; SEQ ID NOS: 1 and 2, respectively. Threonine 88 for Cripto-1 and Cripto-3 is shown in bold. The signal sequence for Cripto-1 (comprising residues 1-30 of SEQ ID NO: 1) is shown underlined.

FIG. 2. Schematic representation of the Cripto expression constructs described. Constructs were generated as described in EXAMPLE 3.

Figure 3:
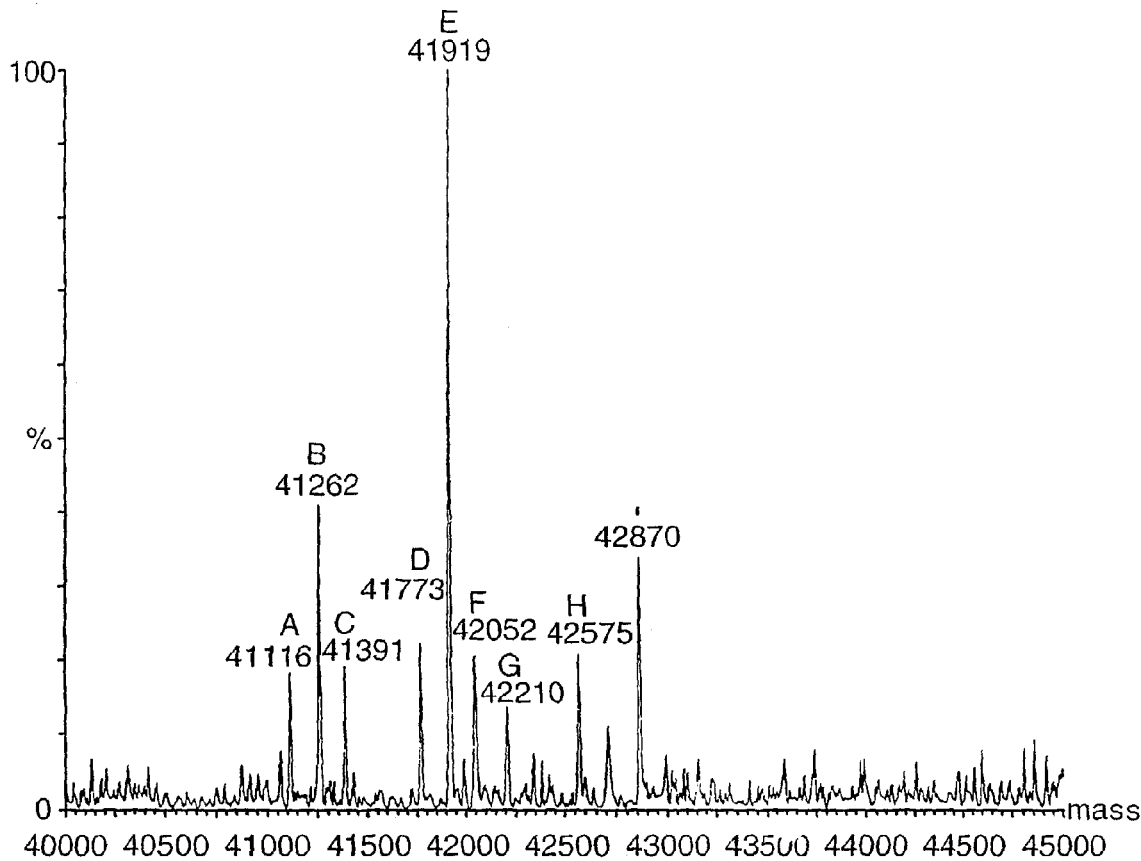

FIG. 3. Electrospray mass spectrometric analysis of N-deglycosylated CR(CC)-Fc protein. The CR(CC)-Fc glycoprotein in phosphate-buffered saline, pH 7.6, 5 mM EDTA was reduced in 5 mM dithiothreitol (DTT) at room temperature for 6 hrs and then treated with 150 milliunits of PNGase F per mg of CR(CC)-Fc at 37° C. for 16 hrs. The N-deglycosylated product was analyzed by ESI-MS analyses on a triple quadrupole instrument (Quattro II, Micromass, Manchester, UK).

Figure 4:
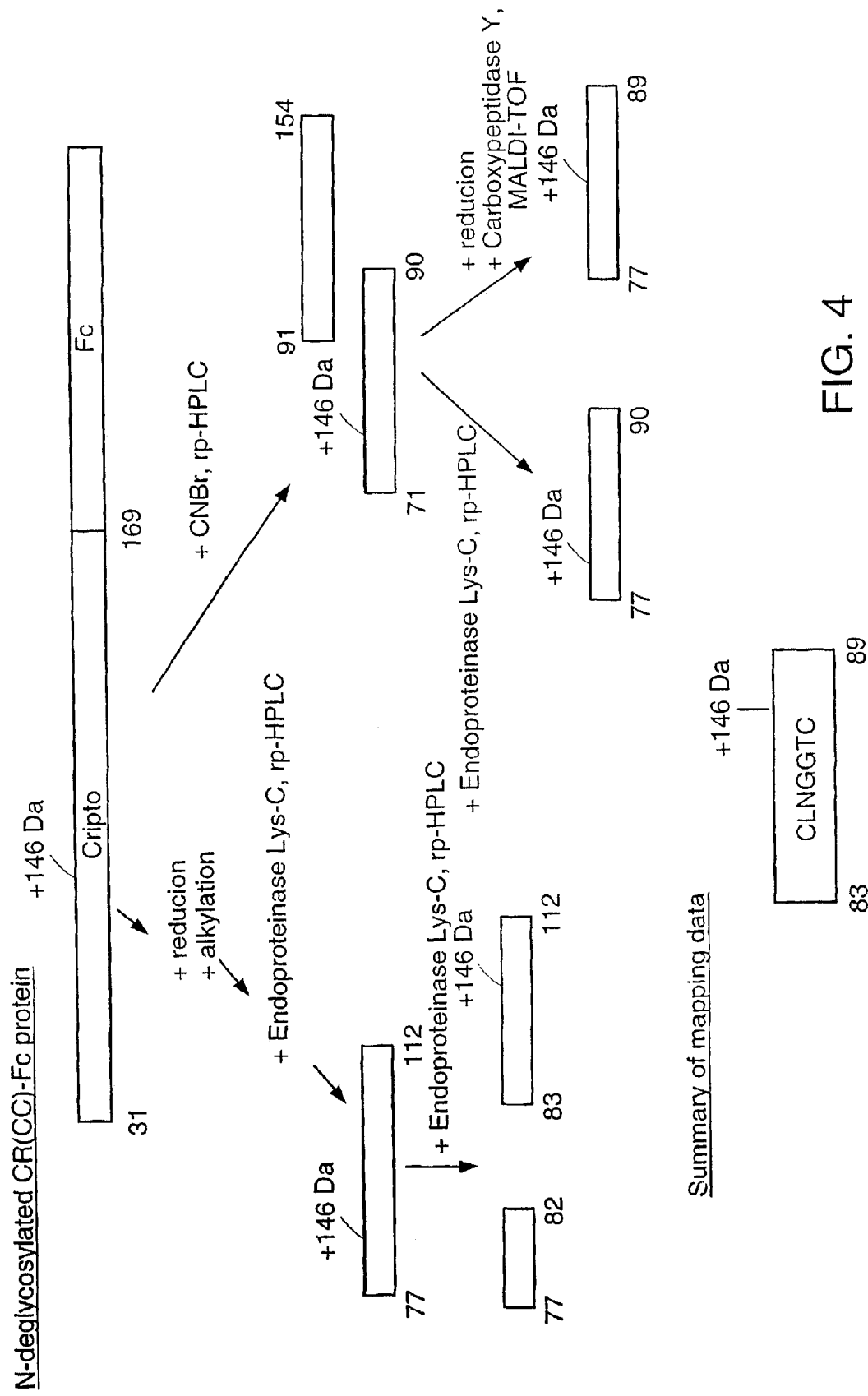

FIG. 4. Schematic of peptide mapping and mass spectrometric analysis of CRIPTO protein. The N-deglycosylated CR(CC)-Fc was digested with either endoproteinase Lys-C, CNBr and carboxypeptidase Y as described in EXAMPLE 2. Cripto peptides from the digests were separated by rp-HPLC and analyzed by mass spectrometry.

Figure 5:
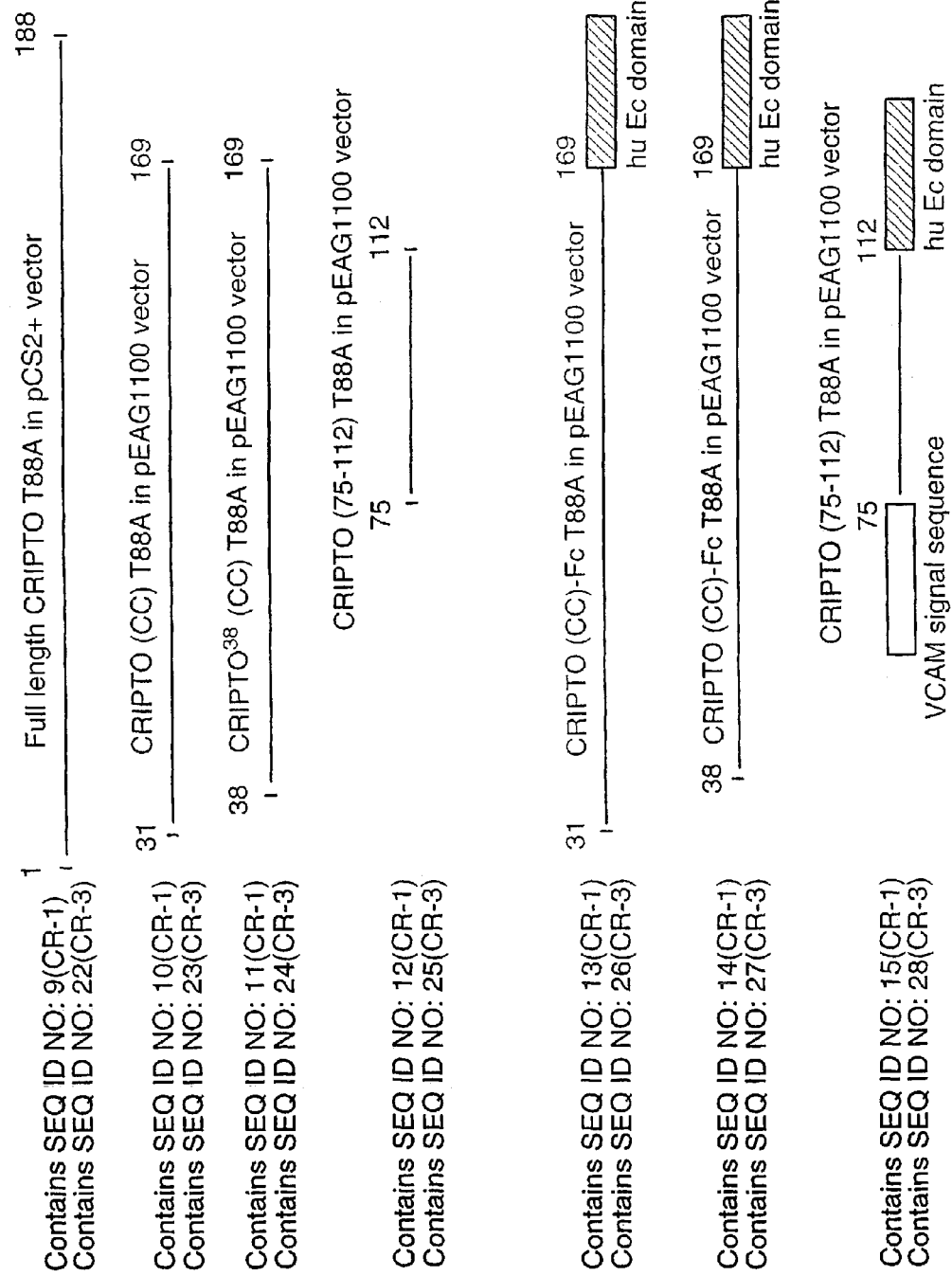

FIG. 5. Schematic representation of the mutant Cripto expression constructs described. Constructs were generated as described in EXAMPLE 3.

Figure 6:
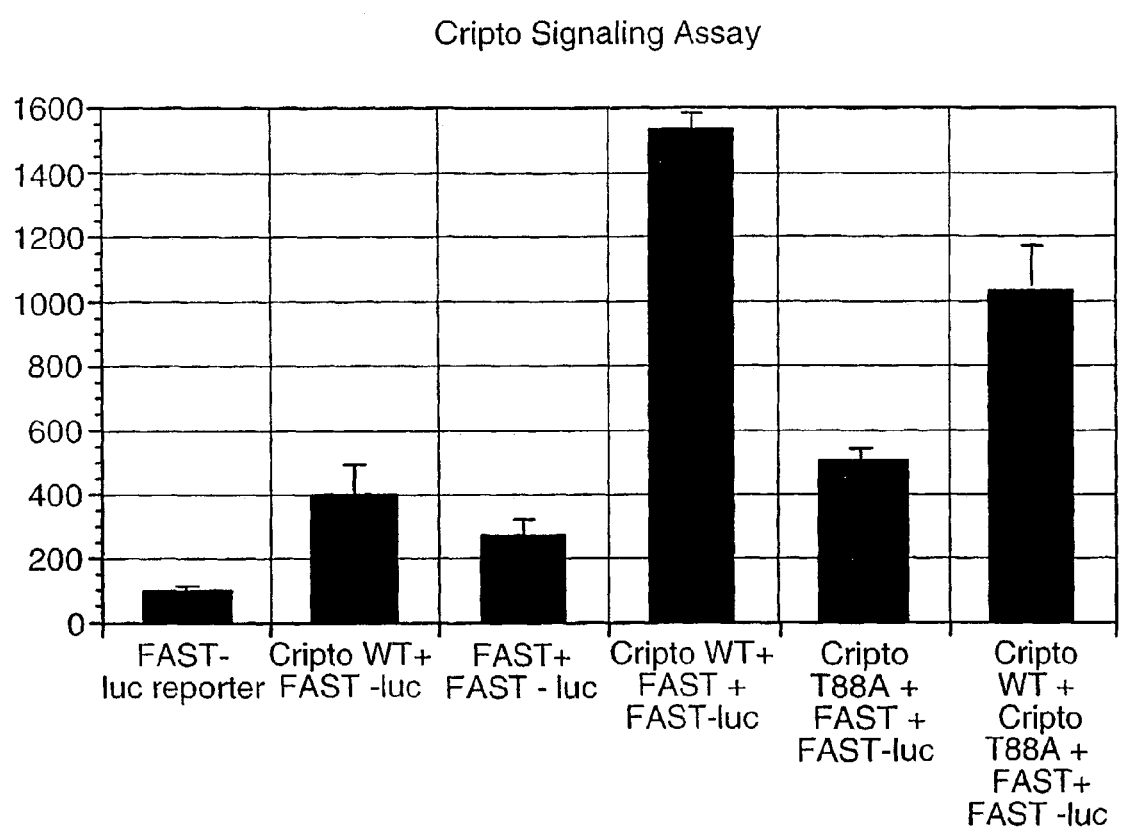

FIG. 6. Cripto signaling assay. The biological activity of human Cripto-1 (SEQ ID NO: 1) and human Cripto-1 T88A (SEQ ID NO: 5) were assessed in F9 Cripto KO cells transfected with the FAST regulatory element-luciferase reporter construct as described in EXAMPLE 4. F9 Cripto KO cells (6.5×10$^5$ cells/well) were transfected with equal amounts of FAST, FAST regulatory element-luciferase reporter DNA, and in the absence or presence of Cripto full length wild-type DNA, in the absence or presence of Cripto T88A mutant full length DNA, and to assess blocking activity with equal amounts of wild type CR and CR T88A cDNAs. Forty eight hours following transfection, cells were lysed with LucLite (Packard Instrument Company) and luciferase activity measured in a luminescence counter.

DETAILED DESCRIPTION OF THE INVENTION

It is a discovery of the present invention that human CRIPTO expressed in mammalian cells is modified with a fucose group at a "fucosylation site" and that this modification is important for biological activity. CRIPTO polypeptides with alterations within the fucosylation site can block CRIPTO function, thus allowing these CRIPTO variants to serve as functional mutants.

Sequence Listing Brief Descriptions

SEQ ID NO:1—full length CRIPTO-1 (CR-1)—amino acid residues 1-188.

SEQ ID NO:2—full length CRIPTO-3 (CR-3)—amino acid residues 1-188
SEQ ID NO:3—amino acid residues 31-169 CR-1
SEQ ID NO:4—amino acid residues 38-169 CR-1
SEQ ID NO:5—amino acid residues 75-112 CR-1
SEQ ID NO:6—amino acid residues 31-169 of CR-1-Fc
SEQ ID NO:7—amino acid residues 38-169 CR-1-Fc
SEQ ID NO:8—amino acid residues 75-112 CR-1-Fc
SEQ ID NO:9—full length CR-1+T88A
SEQ ID NO:10—amino acid residues 31-169 CR-1+T88A
SEQ ID NO:11—amino acid residues 38-169 CR-1+T88A
SEQ ID NO:12—amino acid residues 75-112 CR-1+T88A
SEQ ID NO:13—amino acid residues 31-169 CR-1-Fc+T88A
SEQ ID NO:14—amino acid residues 38-169 CR-1-Fc+T88A
SEQ ID NO:15—amino acid residues 75-112 CR-1-Fe+T88A
SEQ ID NO:16—amino acid residues 31-169 CR-3
SEQ ID NO:17—amino acid residues 38-169 CR-3
SEQ ID NO:18—amino acid residues 75-112 CR-3
SEQ ID NO:19—amino acid residues 31-169 CR-3-Fc
SEQ ID NO:20—amino acid residues 38-169 CR-3-Fc
SEQ ID NO:21—amino acid residues 75-112 CR-3-Fc
SEQ ID NO:22—full length CR-3+T88A
SEQ ID NO:23—amino acid residues 31-169 CR-3+T88A
SEQ ID NO:24—amino acid residues 38-169CR-3+T88A
SEQ ID NO:25—amino acid residues 75-112 CR-3+T88A
SEQ ID NO:26—amino acid residues 31-169 CR-3-Fc+T88A
SEQ ID NO:27—amino acid residues 38-169 CR-3-Fc+T88A
SEQ ID NO:28—amino acid residues 75-112 CR-3-Fc+T88A
SEQ ID NO:29—primer NEW-547
SEQ ID NO:30—primer NEW-587
SEQ ID NO:31—primer NEW-588
SEQ ID NO:32—primer NEW-423
SEQ ID NO:33—primer NEW-670
SEQ ID NO:34—primer NEW-658
SEQ ID NO:35—primer NEW-659
SEQ ID NO: 36—nucleic acid sequence encoding CR-1
SEQ ID NO: 37—nucleic acid sequence encoding CR-3

Selected Definitions

Terms used herein, including "DNA", "gene", "polypeptide", "amino acid" and the like are used in the sense of their art-recognized meanings in the fields of cell biology, cell culture, molecular biology, transgenic biology, microbiology, recombinant DNA or genetic engineering, and immunology. Such meanings are determined by consultation of one or more of the following widely available texts: *Molecular Cloning, A Laboratory Manual*, 2nd Ed. (Sambrook, Fritsch and Maniatis, eds.), Cold Spring Harbor Laboratory Press, 1989; *DNA Cloning*, Volumes I and II (Glover, ed.), 1985; *Oligonucleotide Synthesis* (Gait, ed.), 1984; U.S. Pat. No. 4,683,195, Mullis et al., invs.; *Nucleic Acid Hybridization* (Hames & Higgins, eds.). 1984; *Transcription and Translation* (Hames & Higgins, eds.), 1984; *Culture of Animal Cells* (Freshney), Alan R. Liss, publ., 1987; *Immobilized Cells and Enzymes* (IRL Press), 1986; *A Practical Guide to Molecular Cloning* (Perbal), 1984; *Current Protocols in Molecular Biology*, Wiley & Sons, publ., 1989; *Methods in Enzymology*, Academic Press, New York N.Y. (especially Volumes 154 and 155); *Gene Transfer Vectors for Mammalian Cells* (Miller and Calos, eds.), Cold Spring Harbor Laboratory Press, 1987; *Immunochemical Methods in Cell and Molecular Biology*

(Mayer and Walker, eds.), Academic Press, London, 1987; *Handbook of Experimental Immunology*, Volumes I-IV (Weir and Blackwell, eds.), 1986; and, *Manipulating the Mouse Embryo*, Cold Spring Harbor Laboratory Press, 1986.

As used herein a "CRIPTO polypeptide", is any naturally occurring CRIPTO protein or polypeptide including for example CRIPTO-1 as depicted in SEQ ID NO: 1 or CRIPTO-3 as depicted in SEQ ID NO: 2, or fragment or variant thereof. Variants can differ from a naturally occurring CRIPTO polypeptide in amino acid sequence or in ways that do not involve sequence, or both. Variants in amino acid sequence are produced when one or more amino acids in naturally occurring CRIPTO polypeptide is substituted with a different natural amino acid, an amino acid derivative or non-natural amino acid. Particularly preferred substitution variants include naturally occurring CRIPTO polypeptides, or biologically active unique fragments thereof, whose sequences differ from the wild type sequence by one or more conservative amino acid substitutions, which typically have minimal influence on the secondary structure and hydrophobic nature of the protein or peptide. Conservative substitutions typically include the substitution of one amino acid for another with similar characteristics, such as substitutions within the following groups: valine, glycine; glycine, alanine; valine, isoleucine; aspartic acid, glutamic acid; asparagine, glutamine; serine, threonine; lysine, arginine; and phenylalanine, tyrosine. Other conservative substitutions are those which meet the criteria for an "accepted point mutation" as defined in the *Atlas of Protein Sequence and Structure* (Dayhoff et al., eds.), 1978. See also PCT publication no. WO97/44460. Variants can be naturally-occurring, or produced through synthetic or molecular engineering techniques. Those of skill in the art will understand and appreciate that an engineered CRIPTO variant can provide advantageous properties, e.g., in facilitating purification, improving stability, modulating a biological function, or the like.

As used herein a "CRIPTO mutant" is a CRIPTO polypeptide or CRIPTO variant in which at least one amino acid from a CRIPTO polypeptide is substituted with another amino acid which is different from that present in the CRIPTO polypeptide and which can block or inhibit CRIPTO binding to a CRIPTO binding partner. In one embodiment, the amino acid substitution includes but is not limited to amino acid residues 86, 87 or 88 of the amino acid sequence of the CRIPTO polypeptide or protein. The CRIPTO mutant binding blocks or inhibits cellular responses which would otherwise be triggered by ligation of the CRIPTO binding partner with CRIPTO. In a preferred embodiment the CRIPTO mutant can inhibit or block CRIPTO binding to a CRIPTO binding partner by about 20, 30, 40 or 50 percent.

As used herein a "functional fragment" of a mutant CRIPTO polypeptide is a fragment of the polypeptide that is shorter than the full length polypeptide and has the ability to block or inhibit CRIPTO binding to a CRIPTO binding partner. In a preferred embodiment the functional fragment can inhibit or block CRIPTO binding to a CRIPTO binding partner by about 20%, 30%, 40% or 50%. Methods of establishing whether a fragment of an mutant CRIPTO polypeptide is functional are known in the art. For example, fragments of interest can be made by either recombinant, synthetic, or proteolytic digestive methods. Such fragments can then be isolated and tested for their ability to block or inhibit CRIPTO binding to a CRIPTO binding partner by procedures by methods known to those of skill in the art including competitive blocking experiments.

As used herein "inhibiting the growth of a tumor cell" means a molecule that can inhibit or block the growth or proliferation of a tumor cell by about 20%, alternatively about 30%, about 40% or preferably by about 50% as measured by techniques known to those of skill in the art including monitoring a tumor by radiological imaging techniques including computed tomography (CT), which is typically used to monitor diseased areas in the chest, abdomen, pelvis and head; magnetic resonance imaging (IRI), which is typically used to monitor diseased areas in the abdomen, pelvis, brain, spine, other bones; mammograms which is typically used to monitor diseased areas in the breast. Examples of tumor markers known to those of skill in the art include carcinoembryonic antigen (CEA) often used to monitor patients with colorectal cancer for disease progression as well as patients with for example gastrointestinal or breast tumors with documented elevated levels of CEA at diagnosis or later in their disease course: CA19-9 most commonly used to monitor patients with pancreatic cancer but also elevated in colorectal cancer; CA15-3 and CA27.29 which is often elevated in patients with breast cancer (CA means cancer antigen).

As used herein a "heterologous" means derived from a distinct entity from that of the rest of the entity to which it is being compared. Examples of heterologous a polynucleotide introduced by genetic engineering techniques into a plasmid or vector derived from a different species is a heterologous polynucleotide a DNA binding domain, a histidine tag; epitope tag sequence As used herein an "Fc region" refers to the part of an antibody comprising the CH2, CH3 and hinge regions but lacking the antigen binding sites.

As used herein "fucosylation site" is an amino acid sequence which can be defined experimentally using mass spectrometry by the identification of a 146 Dalton mass addition characteristic of a fucose group on a particular amino acid residue.

As used herein a CRIPTO polypeptide has "activity" if it has at least one of the following properties: (i) it induces phosphorylation of smad2; (ii) it modulates FAST dependent activity as measured by the induction of a FAST regulatory element-luciferase reporter construct; (iii) stimulates migration of mammary gland cell lines in Boydon chamber migration assay; (iv) stimulate branching of mammary epithelial cells in collagen gel (see Ebert et al., Exp Cell Res 25: 223-229, 2000). A mutant CRIPTO that blocks CRIPTO binding to a CRIPTO binding partner would show decreased levels of these activities relative wild type CRIPTO. For example, a CRIPTO mutant as defined herein would result in 20%, preferably 30% and more preferably 50% less phosphorylation of SMAD2 as compared to a control. Alternatively a mutant CRIPTO that blocks CRIPTO binding to a CRIPTO binding partner modulates FAST dependent activity as measured by the inhibition of a PAST regulatory element, ie luciferase reporter by 20%, preferably 30% more preferably 50% as compared to a control.

A used herein "defucosylation modification" mean the chemical or enzymatic removal of a fucose group. As an example, the fucose on the Thr 88 on the CRIPTO polypeptide of the present invention as used herein can be removed enzymatically by fucosidase alternatively the fucose on the Thr 88 on the CRIPTO polypeptide of the present invention can be chemically removed by acid treatment.

As used herein hybridization of the oligonucleotide probe to a nucleic acid sample typically is performed under "stringent conditions". Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical, rather than identical, then it is useful to first establish the lowest temperature at which only homologous hybridization occurs with a particular concentration of salt (e.g. SSC or SSPE). Then, assuming that 1% mismatch results in a 1° C. decrease in the Tm, the temperature of the final wash in the hybridization reaction is reduced accordingly (for example, if the sequences have >95% identity with the probe are sought, the final wash temperature is decreased 5° C.). In practice, the change in the Tm can be between 0.5 C and 1.5 C per 1% mismatch. Stringent conditions involve hybridization at 68° C. in 5×SSC/5× Denhardt's solution/1.0% SDS, and washing in 0.2×SSC/0.1% SDS at room temperature. "Moderately stringent conditions" include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., supra; and Ausubel et al., supra.

Therapeutic Uses of the Compounds of the Invention

The invention provides for treatment or prevention of various diseases and disorders by administration of pharmaceutical compositions of the invention.

In specific embodiments, pharmaceutical compositions of the invention are used to treat or prevent undesired cell proliferation in a subject. In an embodiment of interest, the pharmaceutical compositions of the invention can be used therapeutically to inhibit or block growth of tumors which depend on CRIPTO protein for growth. In a particular aspect the disease or condition associated with undesired cell proliferation is cancer. In a preferred embodiment the cancer is selected from the non-limiting group consisting of breast cancer, ovarian cancer, renal cancer, colorectal cancer, uterine cancer, prostate cancer, lung cancer, bladder cancer, central nervous system cancer, melanoma or leukemia.

Pharmaceutical Composition

The invention provides methods of treatment by administration to a subject of an effective amount of a pharmaceutical composition of the invention. In a preferred aspect, the pharmaceutical composition is substantially purified. The term "subject" as used herein is taken to mean any mammal to which a pharmaceutical composition of the present invention can be administered. Subjects specifically intended for treatment with the method of the invention include humans, as well as nonhuman primates, sheep, horses, cattle, goats, pigs, dogs, cats, rabbits, guinea pigs, hamsters, gerbils, rats and mice.

The pharmaceutical composition of the present invention are preferably tested in vitro and then in vivo for the desired result, prior to use in humans. In various specific embodiments, in vitro assays can be carried out with representative cells of cell types (e.g. breast cancer cells) involved in a subject's disorder to determine if CRIPTO mutant has a desired effect upon such cell types, e.g. as described in Example 4

In general, compounds of the invention are suspended, dissolved or dispersed in a pharmaceutically acceptable carrier or excipient. The resulting pharmaceutical composition does not adversely affect the subject's homeostasis, particularly electrolyte balance. Thus, an exemplary carrier comprises normal physiologic saline (0.15M NaCl, pH 7.0 to 7.4). Other acceptable carriers are well known in the art and are described, for example, in *Remington's Pharmaceutical Sciences*, Gennaro, ed., Mack Publishing Co., 1990. Acceptable carriers can include biocompatible, inert or bioabsorbable salts, buffering agents, oligo- or polysaccharides, polymers, viscosity-improving agents, preservatives, and the like. In some embodiments, the term "carrier" encompasses liposomes and the HIV-1 tat protein (See Chen et al., Anal. Biochem. 227: 168-175, 1995) as well as any plasmid and viral expression vectors.

Any CRIPTO mutant of this invention can be used in the form of a pharmaceutically acceptable salt. Suitable acids and bases which are capable of forming salts with the polypeptides, nucleic acids and vectors of the present invention are well known to those of skill in the art, and include inorganic and organic acids and bases.

CRIPTO mutants of the invention are dispersed in the carrier to concentrations sufficient to deliver to the subject a therapeutically effective amount of the compound, which is an amount sufficient to produce a detectable, preferably medically beneficial effect in the subject. Medically beneficial effects would include preventing, delaying or attenuating deterioration of, or detectably improving, the subject's medical condition. It is expected that the concentration or amount of a CRIPTO mutant that will produce a medically beneficial effect will vary considerably with the circumstances in which the invention is practiced. An effective amount can be determined by an ordinarily skilled physician or other practitioner through no more than routine experimentation. As an example, an indication of the status of undesired cell proliferation can be monitored with one or more routine laboratory tests which measure, for example, the CEA, CA19-9, CA15-3, CA27.29 or CA15-3 levels as described supra. The parameters measure by these tests can be used by a physician to assess disease progression or regression.

In some embodiments, a CRIPTO mutant is formulated in a liposome delivery system, including without limitation any of a variety of unilamellar vesicles, multilamellar vesicles, or stable plurilamellar vesicles, all of which can prepared and administered according to methods well known to those of skill in the art, for example in accordance with the teachings of U.S. Pat. Nos. 5,169,637, 4,762,915, 5,00,958 or 5,185,154. In addition, it may be desirable to express the novel polypeptides of this invention, as well as other selected polypeptides, as lipoproteins, in order to enhance their binding to liposomes. As an example, treatment of a disease or condition associated with undesired cell proliferation with liposome-encapsulated CRIPTO mutant may be performed in vivo by introducing a CRIPTO mutant into a patient in need of such treatment using liposomes. The liposomes can be delivered via catheter to the subjects artery. The encapsulated protein may be tested in vitro for any effect on inhibiting undesired cell proliferation.

Routes of Administration

The compounds of the invention may be administered in any manner which is medically acceptable. Depending on the specific circumstances, local or systemic administration may be desirable. Preferably, the compound is administered via a parenteral route such as by an intravascular, intravenous, intraarterial, subcutaneous, intramuscular, intratumor, intraorbital, intraventricular, intraperitoneal, subcapsular, intracranial, intraspinal, or intranasal injection, infusion or inhalation. The compound also may be administered by implantation of an infusion pump, or a biocompatible or bioerodable sustained release implant, or by installation of a catheter (e.g., in a renal artery), into the subject. Alternatively, certain compounds of the invention, or formulations thereof, may be appropriate for oral or enteral administration. Still other compounds of the invention will be suitable for topical administration.

Treatment Regimes

Determining appropriate dosage and frequency of treatment with any particular CRIPTO mutant to be administered to an individual is within the skills and clinical judgement of ordinary practitioners. The general dosage and treatment schedule is established by preclinical and clinical trials, which involve extensive but routine studies to determine the optimal administration parameters of the compound. Even after such recommendations are made, the practitioner will often vary these dosages for different individuals based on a variety of considerations, such as the individual's age, medical status, weight, sex, and concurrent treatment with other pharmaceuticals. Determining the optimal dosage and administration regime for each CRIPTO mutant is a routine matter for those of skill in the pharmaceutical and medical arts.

EXAMPLES

Example 1

Production of Recombinant Cripto

A. Expression and Purification of Human CriptoCC-Fc in CHO Cells

An expression plasmid designated pSGS480 was constructed by sub-cloning a cDNA encoding human Cripto amino acids residues Methionine 1 to Serine169 of SEQ ID NO: 1 fused to human $IgG_1$ Fc domain (CR(CC)-Fc: SEQ ID NO: 6) into vector pEAG1100 (constructs are shown schematically in FIG. 1). The vector pEAG1100 is a derivative of GIBCO-BRL Life Technologies plasmid pCMV-Sport-beta-gal, whose use in CHO transient transfections was described by Schifferli et al., 1999, Focus 21: 16. It was made by removing the reporter gene beta-galactosidase NotI fragment from the plasmid pCMV-Sport-Betagal (catalog number 10586-014) as follows: The plasmid was digested with NotI and EcoRV, the 4.38 kb NotI vector backbone fragment was gel-purified and ligated. Ligated DNA was transformed into competent *E. coli* DH5alpha. pEAG1100 was isolated as a plasmid containing the desired recombinant from an isolated single colony. The sequence of pEAG1100 spanning the promoter, polylinker, and transcription termination signal was confirmed.

Plasmid pSGS480 was transiently transfected into CHO cells and the cells were grown at 28° C. for 7 days. The presence of CR(CC)-Fc protein in these cells and the conditioned media was examined by Western blot analysis. For Western blot analysis, conditioned media and cells from Cripto transfected cells were subjected to SDS-PAGE on 4-20% gradient gels under reducing conditions, transferred electrophoretically to nitrocellulose, and the Cripto detected with a rabbit polyclonal antiserum raised against a Cripto 17-mer peptide (comprising residues 97-113 of SEQ ID NO: 1)-keyhole limpet hemocyanin conjugate. After centrifugation to remove the cells, Western blot analysis showed that the CR(CC)-Fc protein was efficiently secreted into the conditioned media (supernatant). The supernatant was applied to a Protein A-Sepharose (Pharmacia), and bound protein was eluted with 25 mM sodium phosphate pH 2.8, 100 mM NaCl. The eluted protein was neutralized with 0.5 M sodium phosphate pH 8.6, and analyzed for total protein content from absorbance measurements at 240-340 nm and for purity by SDS-PAGE. The eluted protein was filtered through a 0.2 micron filter, and stored at −70° C.

N-terminal sequencing was carried out on a Perkin-Elmer Applied Biosystems (PE-ABD) Procise HT sequencer, run in the pulsed liquid mode. The resulting PTH amino acids were separated using a PE ABD 140C Microgradient System with a PTH C18 2.1×250 mm column and analyzed on-line using a PE ABD 785A programmable absorbance detector. Data was analyzed using ABI 610A data analysis software. Sequencing identified a single N-terminus: $L_{31}$GHQEFAR.

B. Expression and Purification of Human Cripto(75-112)-Fc in CHO Cells

An expression plasmid designated pSGS422, was constructed by sub-cloning a cDNA encoding human VCAM-1 signal peptide fused to human Cripto-1 residues 75-112 of SEQ ID NO: 1 fused to human $IgG_1$ Fc domain (CR(75-112)-Fc, SEQ ID NO: 8) in vector pEAG1100, essentially as described above for CR(CC)-Fc (FIG. 2). Plasmid pSGS422 was transiently transfected into CHO cells. The CR(75-112)-Fc protein was efficiently secreted into the supernatant and purified from the conditioned media by chromatography on Protein A as described above for CR(CC)-Fc.

Example 2

Characterization of O-linked Glycosylation on Cripto

Purified recombinant hu CR(CC)-Fc and recombinant hu CR(75-112)-Fc were characterized by mass spectrometry before and after N-deglycosylation. Peptide mapping by treatment with enzymes or cyanogen bromide yielded fragments that were separated by reversed phase(rp)-HPLC and characterized by MALDI and electrospray (ESI) mass spectrometry. Biochemical characterization by peptide mapping, mass spectrometry and glycosidase treatment identified Asn-79 as an being an N-linked glycosylation site with ~90% occupancy, and Ser-40 and Ser-161 as being O-linked glycosylation sites with ~80% and ~40% occupancy respectively. In addition, as detailed below, Cripto was modified with a single O-linked fucose at position Thr 88.

A A. PNGase treatment of Cripto

PNGase F was purchased from Oxford Glycosciences. The CR(CC)-Fc glycoprotein in phosphate-buffered saline, pH 7.6, 5 nM EDTA was reduced in 5 mM dithiothreitol (DTT) at room temperature for 6 hrs and then treated with 150 milliunits of PNGase F per mg of CR(CC)-Fc at 37° C. for 16 hrs. The N-deglycosylated product was analyzed by ESI-MS analyses on a triple quadrupole instrument (Quattro II, Micromass, Manchester, UK).

Electrospray ionization mass spectrometry data for the N-deglycosylated and reduced CR(CC)-Fc showed a number of species with masses ranging from 4116 to 42870 Da (FIG. 3). A number of these species had measured masses that matched the predicted mass for CR(CC)-Fc starting at residue 31 and being, modified with O-linked glycans (HexNAc-Hex-NeuAc). In contrast, a number of species were identified for which the masses did not agree with any available prediction, although the difference in mass of 146 Da for each species was consistent with the addition of a fucose group (FIG. 3).

The deconvoluted mass spectrum of the N-deglycosylated and reduced CR(75-112)-Fc protein also showed a number of species with masses 146 Da higher than predicted, consistent with a fucose modification.

B. Endoproteinase Lys-C Peptide Mapping

The identity and attachment position of the apparent 146 Da post-translational modification within the human Cripto sequence was further determined using a combination of peptide mapping and mass spectrometry. FIG. 4 shows schematically the strategy used and the results.

The CR(CC)-Fc sample used for the following peptide mapping experiments was reduced with DTT as described above, and after adjusting the sample to 6 M guanidine, reduced with an additional 10 mM DTT for 35 min at 45° C., and alkylated with 30 mM iodoacetamide at room temperature in the dark for 30 min. The mass of the intact, N-deglycosylated, reduced and fully alkylated protein was still 146 Da higher than predicted. This indicated that the +146 Da was not associated with a cysteine residue.

The reduced and alkylated CR(CC)-Fc material was digested in 1 M urea, 200 mM Tris-HCl, pH 8.5 with endoproteinase Lys-C (Achromobacter lyticus; WAKO) at a 1:10 enzyme to substrate ratio, for 16 hours at room temperature. The peptides from the endoproteinase Lys-C digest of reduced and alkylated-CR(CC)-Fc sample were separated by reversed-phase(rp)-HPLC on a YMC $C_{18}$ column using a Waters Alliance System at a flow rate of 0.05 ml/min with a 120 minute 0-45% solvent B gradient (solvent A: 0.1% TFA; solvent B: 0.085% TFA/75% acetonitrile), and analyzed on-line by mass spectrometry (Micromass Quattro II triple quadrupole instrument). The data showed that the +146 Da modification was associated with an endoproteinase Lys-C generated Cripto peptide comprising residues 77-112. Further localization of the +146 modification on Cripto came from a preparative endoproteinase Lys-C digest of reduced and alkylated-CR(CC)-Fc. Peptides were analyzed by rp-HPLC on a YMC Cis column and eluted with a gradient of solvent B as follows: 0-10% B in 10 minutes; 10-28% B from 10-46 minutes; isocratic at 28% from 46-70 minutes; 28-50% B from 70-145 minutes; 50-100% B from 145-155 minutes. Each Cripto peptide (or mixture) was collected and analyzed by MALDI mass spectrometry (Voyager DE STR instrument, Perseptive Biosystems) using α-cyano-4 hydroxy-cinnamic acid as the matrix. Eluate (2 µl) covering a specified peak were applied to the MALDI plate and allowed to partially air-dry. To each spot, 0.7 µL of matrix (10 mg alpha cyano-4 hydroxy-cinamic acid/mL 0.1% trifluoroactic acid, 50% acetonitrile) were added and allowed to air-dry completely. Samples were analyzed in the linear mode. In addition, to the 77-112 Cripto peptide seen previously in the EndoLys-C digests of CR(CC)-Fc, two peptides resulting from this 77-112 fragment undergoing a non-specific cleavage event were also observed. From this analysis, the 77-82 peptide was found to have the predicted mass, and the 146 Da mass addition was further localized onto a Cripto peptide corresponding to residues 83-112 (FIG. 4). The identity of this peptide was confirmed by N-terminal Edman sequencing.

C. Cyanogen Bromide Mapping

Further evidence for the site of the 146 Da modification was obtained by treating the non-reduced CR(CC)-Fc with cyanogen bromide (CNBr). The PNGase-treated CR(CC)-Fc prepared as above but without reduction, was resuspended in 200 µL of 70% formic acid. A solution of 10 M CNBr in acetonitrile was added to the reaction mixture to a final concentration of 1 M. The sample was held at room temperature, in the dark, for 24 hours. The CNBr treated Cripto peptides were fractionated by rp-HPLC on a Vydac $C_4$ column using the following gradient of Solvent A, 0.1% TFA, Solvent B 0.085% TFA, 75% acetonitrile: 0-20% B from 0-10 minutes; 20-75% B from 10-120 minutes; 75-100% B from 120-130 minutes. CNBr cleavage yields a fragment corresponding to predicted residues 71-90 disulfide-linked to residues 91-154 (FIG. 4). After reduction, a molecular mass as measured by MALDI mass spectrometry showed the mass of peptide 71-90 to be 146 dalton higher than predicted.

The CNBr-treated CR(CC)-Fc fragments were further digested with endoproteinase Lys-C in 1 M urea at an estimated enzyme:substrate ratio of 1:5 for 18 hours at room temperature. The peptides from the CNBr/endoproteinase Lys-C digest of CR(CC)-Fc sample were separated by reversed-phase(rp)-HPLC on a YMC $C_{18}$ column as described above. The data confirmed that the +146 Da modification was associated with a CNBr/endoproteinase Lys-C generated Cripto peptide comprising residues 83-90.

The CNBr fragment comprising residues 71-90 disulfide-linked to residues 91-154 was reduced with 5 mM DTT and treated with carboxypeptidase Y (Boehringer Mannheim). Portions of the digest were analyzed at 10 minute intervals by MALDI mass spectrometry. The results showed that the C-terminal homoserine lactone (Met converted to homoserine lactone after CNBr cleavage) of peptide 71-90 could be removed without loss of the extra 146 Da (FIG. 4).

The endoproteinase Lys-C digest of CR(CC)-Fc (Example 2, part B) localized the 146 Da modification to a Cripto peptide comprising residues 83-112. The CNBr/endoproteinase Lys-C digests of CR(CC)-Fc (Example 2, part C) localized the 146 Da modification to a Cripto peptide comprising residues 71-90. Taken together these two analyses localized the 146 Dalton modification to residues 83-90. The carboxypeptidase Y treatment further localized the 146 dalton modification to Cripto residues 83-89 CLNGGTC. The cysteine residues within this sequence were shown above to be available for alkylation, and are hence not modified by the 146 Dalton. Leucine, glycine are not typically modified. Asn followed by Gly can form a cycle imide with associated loss of 17 Da (loss of $NH_3$), which under basic conditions forms a α or β aspartic acid (addition of OH), resulting in a net increase of 1 Da for this peptide. This leaves Thr 88 as the likely site of modification. It was a discovery of the present invention that Thr 88 has a 146 Da modification which lead us to conclude that Thr 88 was fucosylated. Fucusylation is a rare event in protein modification. The Cripto sequence to which the 146 Da modification was localized fits the motif described for a fucosylation consensus sequence (See Harris et al., Biochemistry 32:6539-6547, 1993) of $C_2XXGGS/TC_3$, where the site is located between the second and third conserved cysteines of the EGF-like sequence, where X is any amino acid and where the fucose is on serine or threonine.

Example 3

Cripto Variant Thr88Ala lacking O-fucose at Position 88

Site specific mutagenesis was used to construct expression vectors capable of expressing cDNAs encoding a Cripto variant having amino acid residue alanine at position 88 rather than threonine. Mutant constructs are shown schematically in FIG. 5.

A. Construction of Mutants

Mutagenesis of human Cripto-1, threonine 88 to alanine (T88A) was accomplished by spliced overlap extension polymerase chain reaction (SOE PCR), reference Stephan Ho et. Al., Gene 77, 1989, pgs 51-59.

The following primers (5' to 3'): were used for mutagenesis, each 44 nucleotides long, are the top and bottom strands creating the Thr88Ala mutation. Asterisks indicate the mutant (Tlr to Ala) codon.

NEW-658:                                          (SEQ ID NO:34)
GCCTGAATGGGGGAG*C*C*TGCATGCTGGGATCCTTTTGTGCCTGC 3'

NEW-659:                                          (SEQ ID NO:35)
GCAGGCACAAAAGGATCCCAGCATGCAG*G*C*TCCCCCATTCAGGC 3'

These oligos change the threonine codon ACC to the codon for alanine, GCC. In designing the mutagenic primers, if a desired mutation did not produce a restriction site change, a mutation was introduced into an adjacent codon to facilitate identification of mutant clones following mutagenesis. The same oligos also make a silent change to the sequence to introduce a BamHI site, changing the glycine 62 codon from GGG to GGA. This new site gave the ability to screen for the mutant clone.

The wild type and T88A Cripto constructs are shown schematically in FIGS. 2 and 5, respectively. The first mutant (CR(CC) T88A, SEQ ID NO: 10), designated pSGS901, was made using template pSGS140, which is a cDNA encoding human Cripto amino acid residues methionine1-serine169 of SEQ ID NO: 1 in pEAG1100 vector for transient transfection. The second mutant (CR(75-112)-Fc T88A), SEQ ID NO: 15), designated pSGS902, was generated from template pSGS422, which is a cDNA encoding human VCAM-1 signal peptide fused to human Cripto-1 residues Serine75 to lysine112 of SEQ ID NO: 1 fused to human IgG$_1$ Fc domain (SEQ ID NO: 8) in vector pEAG1100. The third mutant (CR T88A, SEQ ID NO: 9), designated pSGS903, is made using template pSGS151, which is a cDNA encoding human Cripto amino acid residues 1-188 of SEQ ID NO: 1 in pCS2 vector (See Rapp et al., Genes Dev 8: 1311-1323, 1994; and Turner et al., Genes Dev 8: 1434-1447, 1994) for transient transfection.

There are 2 phases to SOE PCR. Phase I was PCR to produce two products A+B. Product A, the 5' end of the cDNA, was generated by using a top strand oligo of 5' sequence, NEW-547 (SEQ ID NO: 29) for pSGS901 and pSGS903, and NEW-423 (SEQ ID NO: 32) for pSGS902, and the bottom strand mutagenic oligo, NEW-659 (SEQ ID NO: 35). Product B, the 3' end of the cDNA, was generated by using the top strand mutagenic oligo, NEW-658 (SEQ ID NO: 34), and a bottom strand oligo of 3' sequence, NEW-587 (SEQ ID NO: 30) for pSGS901, NEW-588 (SEQ ID NO: 31) for pSGS903, and NEW-670 (SEQ ID NO: 33) for pSGS902.

Phase II of SOE PCR was to make product C, which is the entire mutagenized cDNA. This step used products A+B, which have 44 nucleotides of overlapping sequence, and the 5' top strand and 3' bottom strand oligos discussed in step I above.

Phase I for products A and B for both mutants pSGS901, pSGS902 and pSGS903 was done as follows. PCR was performed with five nanograrms (ng) of template cDNA, 30 picomoles (pmol) each of 5' and 3' oligos, 200 nanomoles (nmol) of each deoxynucleotide (dNTP), 1× cloned Pfu DNA polymerase reaction buffer (2 mM MgCl$_2$), and 2.5 units of PfuTurbo DNA polymerase (Stratagene, cat. #600252) added after a hot start, in 100 microliters (μl) total volume. The reactions required 30 cycles of a 94° C.-1 minute melting step, a 58° C.-1 minute annealing step, a 72° C.-2 minute extension step, followed by one cycle of a 72° C.-7 minute extension. The only exception to this procedure was that the annealing temperature for NEW-423 (SEQ ID NO: 32) was 50° C.

Phase II for mutants pSGS901, pSGS902 and pSGS903 was done as follows. 10 μl each of products A+B were mixed with 200 nmol dNTPs, 30 pmol each of 5' and 3' oligos, Pfu buffer, and 2.5 units of PfuTurbo enzyme added after a hot start. Phase II PCR reaction steps were done as above except for the annealing temperatures. The annealing temperature for pSGS901 and pSGS903 product C PCR is 65° C., and for pSGS902 product C PCR was 55° C. The reactions were run over StrataPrep PCR columns (Stratagene cat# 400771) to purify the products away from any unused oligos. PCR product C for pSGS901 and pSGS902 are was then digested with 60 units of Not1 restriction enzyme for 16 hours at 37° C. PCR product C for pSGS903 was digested with 60 units of Xho1 and Hind111 restriction enzymes for 16 hours at 37° C. The enzyme was extracted once with phenol and chloroform together, once with chloroform, and the DNA was precipitated with ethanol plus 0.3 M sodium acetate pH 5.2 with glycogen as a carrier. The DNA pellet was washed with 70% ethanol plus water and resuspended in 10 mM Tris pH 8. For pSGS901 and pSGS902 constructs, ligations were-now performed between the 20 ng of Not 1 digested product C inserts and 50 ng Not1 digested and calf intestinal phosphatase treated pEAG1100 vector in 10 μl total volume for 16 hours at 16° C. A ligation for pSGS903 was done with 20 ng of the Xho1/Hind111 digested product C and Xho1/Hind111 digested pCS2+vector. Two μl of this reaction was tranformed into 50 μl E. coli DH5α and plated on Luria broth (LB) agar plates with 50 μg/ml ampicillin. Colonies were picked and grown up in 2 mls of LB broth for 16 hours at 37° C. Plasmid DNA was purified using Qiagen miniprep kits, digested with BamH1 for 1.5 hours, and run on agarose gels to visualize which clone contained the silent mutation and thus contained the threonine 88 to alanine change. The sequence of clonal inserts (Cripto and Ig sequences) was checked and confirmed by dideoxy DNA sequencing.

C. Transfection into CHO Cells

Mutations were confirmed by DNA sequencing. After the correct mutant clone was verified, a large scale transient transfection was performed to obtain mutant Cripto protein. This was done using CHO cells (CD-CHO) grown as a suspension culture in spinner flasks. For each liter culture, 2 mg of cDNA was mixed with DMRIE-C (Life Technologies) cationic lipid plus cholesterol solution, in a total volume of 240 mls of serum free media (CD-CHO media, Life Technologies), at room temperature for 15 minutes. Then $1.5 \times 10^9$ CHO cells in 240 mls of the same media was added to the DNA plus DMRIE-C solution, transferred to a 1 liter spinner flask, and grown for 4 hours at 37° C. The cells were then diluted with 520 mls of media, transferred to a 3 liter spinner flask, and grown for 8 days at 28° C. After centrifugation to remove the cells, the conditioned media was filtered over a PES (Nalgene) filter, and frozen at −70° C.

Example 4

Testing the Cripto Antagonists for Function and Modulation of Cripto Signaling Activity Over-expression of Cripto activity can lead to a de-differentiated state promoting mesenchymal cell characteristics, increased proliferation and cell migration (Salomon et al., BioEssays 21: 61-70, 1999; Ciardiello et al., Oncogene 9: 291-298, 1994; and Baldassaire et al., Int. J. Cancer 66:538-543, 1996)—all phenotypes associated with cell transformation seen in neoplasia. Cripto antagonists that block Cripto activity could be therapeutically beneficial and a potential treatment for cancer.

One method of testing the activity of Cripto antagonists and their ability to modulate the Cripto signaling is with a F9-Cripto knock-out (KO) cell line (Minchiotti at al., Mech. Dev. 90: 133-142, 2000). Cripto will stimulate smad2 phosphorylation and the transcription factor FAST in Xenopus embryos, and the activity of the transcription factor FAST can be monitored by measuring the luciferase activity from a FAST regulatory element-luciferase reporter gene (Saijoh et al., Mol. Cell 5:35-47 2000). F9-Cripto KO cells are deleted for the Cripto gene and are thus null for Cripto and Cripto-dependent signaling (Minchiotti at al., Mech. Dev. 90: 133-142, 2000). Cripto signaling can be assessed in the F9 Cripto KO cells by transfecting in Cripto, FAST and the FAST regulatory element-luciferase gene construct (FIG. 6). No Cripto dependent FAST luciferase activity was seen in these cell lines unless Cripto cDNA and FAST cDNA was transfected into them (FIG. 6).

The activity of wild-type and mutant Cripto constructs can be measured by transfecting into the F9 Cripto KO cells. F9 Cripto KO cells ($6.5 \times 10^5$ cells/well) were transfected with equal amounts of FAST, FAST luciferase reporter DNA, and in the absence and presence of Cripto full length wild-type DNA and in the absence and presence of Cripto T88A mutant full length DNA. Total DNA transfected was always 1.0 µg and control vector DNA (pEAG100 or pCS2) was used to bring the total up to 1.0 µg when necessary (transfections were done with Lipofectamine using conditions standard to those with skill in the field, Lipofectamine was purchased from Bethesda Reasearch Labs). Forty eight hours following transfection, cells were lysed with LucLite (a luciferase reporter gene assay kit, Packard Instrument Company) and luciferase activity measured in a luminescence counter. We demonstrated that wild-type Cripto (SEQ ID NO: 1) stimulated FAST regulatory element-luciferase (FAST-luc) reporter activity (FIG. 6, Cripto WT+FAST +FAST-luc reporter, column 4) and that this activity required the presence of both Cripto and FAST (FIG. 6). In contrast, the Thr88Ala Cripto mutant (SEQ ID NO: 9, pSGS903) had little FAST-luciferase activity (FIG. 6, Cripto T88A+FAST +FAST luc reporter, column 5).

A competition experiment in which equal amounts of the CR Thr88Ala mutant cDNA and CR wild-type cDNA were mixed and co-transfected into the F9 KO cells, showed that the ability of wild type CR to stimulate FAST luciferase activity was decreased in the presence of the CR T88A mutant compared to wild type CR alone FIG. 6, the Cripto WT+Cripto T88A+FAST+FAST luc reporter, column 6), indicating that the Thr88Ala mutant acts to antagonize the activity of wild-type Cripto.

Example 5

In vivo Testing of Cripto Antagonists as Potential Anticancer Agents

Cripto antagonists are screened for in vivo activity as potential anticancer agents in mice following standard protocols used by those with skill in the art. Example of such protocols are those listed below and outlined by the National Cancer Institute (NCI) in their "in vivo cancer models screening" protocols, NIH publication number 84-2635 (February 1984).

A. 6 week old nude mice are injected intraperitoneally with 100 µg of anti-LFA3 control antibody (1E6), 100 µg Cripto antagonist-Fc fusion protein (SEQ ID NO: 13) or not injected (control). The animals are then injected subcutaneously with a cancer cell line that expressed cell surface Cripto protein (example: $1 \times 10^6$ GEO colon adenocarcinama cells). The Cripto antagonist and control Ab treated mice are retreated weekly with 100 µg of protein. Tumor size is measured weekly and the volume of the tumor sphere are calculated. Animals are sacrificed when their tumors reached a volume of 2.0 cm$^3$ (16 mm diameter) and any unusual observations recorded. Experiments will be repeated with ranges of Cripto antagonist protein to determine optimal therapeutic profile.

B. 6 week old nude mice (n=10 experimental and n=10 control) weighing approx. (18 g) are implanted with 25 mg fragment of subcutaneous tumor (tumor tissue may be from breast, colon, lung, cervical etc human tumor, tumor tissue expresses Cripto) on day 0. Run bacterial culture on tumor sample, if contaminated discard immediately. On initial treatment day (staging day): Select mice with tumors weighing no less than 100 mg and no more than 700 mg. Randomize and treat by individual body weight. A wide dose range of 1-50 mg/kg is tested. Cripto antagonist protein, Control Antibody, and PBS control animals are injected ip on staging day and continue every 4 days for a total of 3 injections. Body weights and tumor measurements are recorded on initial treatment day (staging day) and selected measurement days. Final evaluation day is the measurement day which yields the optimum (best) tumor weight for t/c % is designated the final evaluation day. End and evaluate experiment.

Equivalents

The invention may be embodied in other specific forms without departing from the spirit or essential characteristics thereof. The foregoing embodiments are therefore to be considered in all respects illustrative of, rather than limiting on, the invention disclosed herein. Scope of the invention thus is indicated by the appended claims rather than by the foregoing description, and all changes which come within the meaning and range of equivalency of the claims are intended to be embraced therein.

What is claimed is:

1. An in vitro method for inhibiting fucosylation-dependent signaling of the CRIPTO polypeptide shown in SEQ ID NO:1 in a tumor cell that expresses said CRIPTO polypeptide, comprising exposing said tumor cell to an effective amount of the CRIPTO polypeptide shown in SEQ ID NO: 1 in which from one to three amino acids are substituted with a different replacement amino acid to form a mutant CRIPTO polypeptide, wherein the position of the from one to three amino acid substitutions are selected from the group consisting of amino acid residues 86, 87 and 88 of the CRIPTO polypeptide.

2. The method of claim 1, wherein the replacement amino acids are selected from the group consisting of an alanine or a glycine.

3. The method of claim 1, wherein the mutant CRIPTO polypeptide comprises an amino acid substitution at position 86.

4. The method of claim 1, wherein the mutant CRIPTO polypeptide comprises an amino acid substitution at position 87.

5. The method of claim 1, wherein the mutant CRIPTO polypeptide comprises an amino acid substitution at position 88.

6. The method of any one of claims 3-5, wherein the replacement amino acid is an alanine or a glycine.

7. An in vitro method for inhibiting fucosylation-dependent signaling of the CRIPTO polypeptide shown in SEQ ID NO:1 in a tumor cell that expresses said CRIPTO polypeptide, comprising exposing said tumor cell to an effective amount of a mutant CRIPTO polypeptide, wherein the mutant CRIPTO polypeptide is encoded by a nucleic acid molecule which hybridizes over its full length to the complement of the nucleic acid molecule of SEQ ID NO:36 (CR-1) under conditions of 68° C. in 5×SSC/5× Denhardt's solution/1.0% SDS followed by washing in 0.2×SSC/0.1% SDS at room temperature, and wherein said mutant CRIPTO polypeptide comprises from one to three amino acid substitutions, wherein the position of the from one to three amino acid substitutions are selected from the group consisting of amino acid residues 86, 87, and 88 of the CRIPTO polypeptide.

* * * * *

SEQUENCE LISTING

<160> NUMBER OF SEQ ID NOS: 37

<210> SEQ ID NO 1
<211> LENGTH: 188
<212> TYPE: PRT
<213> ORGANISM: Homo Sapien

<400> SEQUENCE: 1

Met Asp Cys Arg Lys Met Ala Arg Phe Ser Tyr Ser Val Ile Trp Ile
1               5                   10                  15

Met Ala Ile Ser Lys Val Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Pro Ala Ile Arg Pro Arg Ser Ser
            50                  55                  60

Gln Arg Val Pro Pro Met Gly Ile Gln His Ser Lys Glu Leu Asn Arg
65              70                  75                  80

Thr Cys Cys Leu Asn Gly Gly Thr Cys Met Leu Gly Ser Phe Cys Ala
                85                  90                  95

Cys Pro Pro Ser Phe Tyr Gly Arg Asn Cys Glu His Asp Val Arg Lys
                100                 105                 110

Glu Asn Cys Gly Ser Val Pro His Asp Thr Trp Leu Pro Lys Lys Cys
            115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Phe Met
            165                 170                 175

Leu Val Gly Ile Cys Leu Ser Ile Gln Ser Tyr Tyr
            180                 185

<210> SEQ ID NO 2
<211> LENGTH: 188
<212> TYPE: PRT
<213> ORGANISM: Homo Sapien

<400> SEQUENCE: 2

Met Asp Cys Arg Lys Met Val Arg Phe Ser Tyr Ser Val Ile Trp Ile
1               5                   10                  15

Met Ala Ile Ser Lys Ala Phe Glu Leu Gly Leu Val Ala Gly Leu Gly
            20                  25                  30

His Gln Glu Phe Ala Arg Pro Ser Arg Gly Asp Leu Ala Phe Arg Asp
        35                  40                  45

Asp Ser Ile Trp Pro Gln Glu Pro Ala Ile Arg Pro Arg Ser Ser
            50                  55                  60

Gln Arg Val Leu Pro Met Gly Ile Gln His Ser Lys Glu Leu Asn Arg
65              70                  75                  80

Thr Cys Cys Leu Asn Gly Gly Thr Cys Met Leu Glu Ser Phe Cys Ala
                85                  90                  95

Cys Pro Pro Ser Phe Tyr Gly Arg Asn Cys Glu His Asp Val Arg Lys
                100                 105                 110

Glu Asn Cys Gly Ser Val Pro His Asp Thr Trp Leu Pro Lys Lys Cys
            115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Phe Met
            165                 170                 175

Leu Ala Gly Ile Cys Leu Ser Ile Gln Ser Tyr Tyr
            180                 185

<210> SEQ ID NO 3
<211> LENGTH: 139
<212> TYPE: PRT
<213> ORGANISM: Homo Sapien

<400> SEQUENCE: 3

Leu Gly His Gln Glu Phe Ala Arg Pro Ser Arg Gly Tyr Leu Ala Phe
 1               5                  10                  15

Arg Asp Asp Ser Ile Trp Pro Gln Glu Pro Ala Ile Arg Pro Arg
            20                  25                  30

Ser Ser Gln Arg Val Pro Pro Met Gly Ile Gln His Ser Lys Glu Leu
            35                  40                  45

Asn Arg Thr Cys Cys Leu Asn Gly Gly Thr Cys Met Leu Gly Ser Phe
        50                  55                  60

Cys Ala Cys Pro Pro Ser Phe Tyr Gly Arg Asn Cys Glu His Asp Val
65                  70                  75                  80

Arg Lys Glu Asn Cys Gly Ser Val Pro His Asp Thr Trp Leu Pro Lys
                85                  90                  95

Lys Cys Ser Leu Cys Lys Cys Trp His Gly Gln Leu Arg Cys Phe Pro
            100                 105                 110

Gln Ala Phe Leu Pro Gly Cys Asp Gly Leu Val Met Asp Glu His Leu
            115                 120                 125

Val Ala Ser Arg Thr Pro Glu Leu Pro Pro Ser
            130                 135

<210> SEQ ID NO 4
<211> LENGTH: 129
<212> TYPE: PRT
<213> ORGANISM: Homo Sapien

<400> SEQUENCE: 4

Arg Gly Tyr Leu Ala Phe Arg Asp Asp Ser Ile Trp Pro Gln Glu Glu
 1               5                  10                  15

Pro Ala Ile Arg Pro Arg Ser Ser Gln Arg Val Pro Pro Met Gly Ile
            20                  25                  30

Gln His Ser Lys Glu Leu Asn Arg Thr Cys Cys Leu Asn Gly Gly Thr
            35                  40                  45

Cys Met Leu Gly Ser Phe Cys Ala Cys Pro Pro Ser Phe Tyr Gly Arg
        50                  55                  60

Asn Cys Glu His Asp Val Arg Lys Glu Asn Cys Gly Ser Val Pro His
65                  70                  75                  80

Asp Thr Trp Leu Pro Lys Lys Cys Ser Leu Cys Lys Cys Trp His Gly
                85                  90                  95

Gln Leu Arg Cys Phe Pro Gln Ala Phe Leu Pro Gly Cys Asp Gly Leu
            100                 105                 110

Val Met Asp Glu His Leu Val Ala Ser Arg Thr Pro Glu Leu Pro Pro
            115                 120                 125

Ser

<210> SEQ ID NO 5
<211> LENGTH: 38
<212> TYPE: PRT
<213> ORGANISM: Homo Sapien

```
<400> SEQUENCE: 5

Ser Lys Glu Leu Asn Arg Thr Cys Cys Leu Asn Gly Gly Thr Cys Met
1               5                   10                  15

Leu Gly Ser Phe Cys Ala Cys Pro Pro Ser Phe Tyr Gly Arg Asn Cys
            20                  25                  30

Glu His Asp Val Arg Lys
        35

<210> SEQ ID NO 6
<211> LENGTH: 367
<212> TYPE: PRT
<213> ORGANISM: Homo Sapien

<400> SEQUENCE: 6

Leu Gly His Gln Glu Phe Ala Arg Pro Ser Arg Gly Tyr Leu Ala Phe
1               5                   10                  15

Arg Asp Asp Ser Ile Trp Pro Gln Glu Pro Ala Ile Arg Pro Arg
            20                  25                  30

Ser Ser Gln Arg Val Pro Pro Met Gly Ile Gln His Ser Lys Glu Leu
        35                  40                  45

Asn Arg Thr Cys Cys Leu Asn Gly Gly Thr Cys Met Leu Gly Ser Phe
    50                  55                  60

Cys Ala Cys Pro Pro Ser Phe Tyr Gly Arg Asn Cys Glu His Asp Val
65                  70                  75                  80

Arg Lys Glu Asn Cys Gly Ser Val Pro His Asp Thr Trp Leu Pro Lys
                85                  90                  95

Lys Cys Ser Leu Cys Lys Cys Trp His Gly Gln Leu Arg Cys Phe Pro
            100                 105                 110

Gln Ala Phe Leu Pro Gly Cys Asp Gly Leu Val Met Asp Glu His Leu
        115                 120                 125

Val Ala Ser Arg Thr Pro Glu Leu Pro Pro Ser Val Asp Lys Thr His
    130                 135                 140

Thr Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
    210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Ser Arg Asp Glu Leu Thr Lys Asn Gln Val Ser Leu Thr Cys Leu
        275                 280                 285

Val Lys Gly Phe Tyr Pro Ser Asp Ile Ala Val Glu Trp Glu Ser Asn
    290                 295                 300

Gly Gln Pro Glu Asn Asn Tyr Lys Thr Thr Pro Pro Val Leu Asp Ser
305                 310                 315                 320
```

-continued

Asp Gly Ser Phe Phe Leu Tyr Ser Lys Leu Thr Val Asp Lys Ser Arg
            325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
            355                 360                 365

<210> SEQ ID NO 7
<211> LENGTH: 360
<212> TYPE: PRT
<213> ORGANISM: Homo Sapien

<400> SEQUENCE: 7

Arg Pro Ser Arg Gly Tyr Leu Ala Phe Arg Asp Asp Ser Ile Trp Pro
1               5                   10                  15

Gln Glu Glu Pro Ala Ile Arg Pro Arg Ser Ser Gln Arg Val Pro Pro
            20                  25                  30

Met Gly Ile Gln His Ser Lys Glu Leu Asn Arg Thr Cys Cys Leu Asn
            35                  40                  45

Gly Gly Thr Cys Met Leu Gly Ser Phe Cys Ala Cys Pro Pro Ser Phe
        50                  55                  60

Tyr Gly Arg Asn Cys Glu His Asp Val Arg Lys Glu Asn Cys Gly Ser
65                  70                  75                  80

Val Pro His Asp Thr Trp Leu Pro Lys Lys Cys Ser Leu Cys Lys Cys
            85                  90                  95

Trp His Gly Gln Leu Arg Cys Phe Pro Gln Ala Phe Leu Pro Gly Cys
            100                 105                 110

Asp Gly Leu Val Met Asp Glu His Leu Val Ala Ser Arg Thr Pro Glu
            115                 120                 125

Leu Pro Pro Ser Val Asp Lys Thr His Thr Cys Pro Pro Cys Pro Ala
            130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
            165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
            195                 200                 205

Tyr Asn Ser Thr Tyr Arg Val Val Ser Val Leu Thr Val Leu His Gln
            210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
            245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
            290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
            325                 330                 335

```
Ser Cys Ser Val Met His Glu Ala Leu His Asn His Tyr Thr Gln Lys
        340                 345                 350
Ser Leu Ser Leu Ser Pro Gly Lys
        355                 360

<210> SEQ ID NO 8
<211> LENGTH: 266
<212> TYPE: PRT
<213> ORGANISM: Homo Sapien

<400> SEQUENCE: 8

Ser Lys Glu Leu Asn Arg Thr Cys Cys Leu Asn Gly Gly Thr Cys Met
1               5                   10                  15
Leu Gly Ser Phe Cys Ala Cys Pro Pro Ser Phe Tyr Gly Arg Asn Cys
            20                  25                  30
Glu His Asp Val Arg Lys Val Asp Lys Thr His Thr Cys Pro Pro Cys
        35                  40                  45
Pro Ala Pro Glu Leu Leu Gly Gly Pro Ser Val Phe Leu Phe Pro Pro
    50                  55                  60
Lys Pro Lys Asp Thr Leu Met Ile Ser Arg Thr Pro Glu Val Thr Cys
65                  70                  75                  80
Val Val Val Asp Val Ser His Glu Asp Pro Glu Val Lys Phe Asn Trp
                85                  90                  95
Tyr Val Asp Gly Val Glu Val His Asn Ala Lys Thr Lys Pro Arg Glu
            100                 105                 110
Glu Gln Tyr Asn Ser Thr Tyr Arg Val Val Ser Val Leu Thr Val Leu
        115                 120                 125
His Gln Asp Trp Leu Asn Gly Lys Glu Tyr Lys Cys Lys Val Ser Asn
    130                 135                 140
Lys Ala Leu Pro Ala Pro Ile Glu Lys Thr Ile Ser Lys Ala Lys Gly
145                 150                 155                 160
Gln Pro Arg Glu Pro Gln Val Tyr Thr Leu Pro Pro Ser Arg Asp Glu
                165                 170                 175
Leu Thr Lys Asn Gln Val Ser Leu Thr Cys Leu Val Lys Gly Phe Tyr
            180                 185                 190
Pro Ser Asp Ile Ala Val Glu Trp Glu Ser Asn Gly Gln Pro Glu Asn
        195                 200                 205
Asn Tyr Lys Thr Thr Pro Pro Val Leu Asp Ser Asp Gly Ser Phe Phe
    210                 215                 220
Leu Tyr Ser Lys Leu Thr Val Asp Lys Ser Arg Trp Gln Gln Gly Asn
225                 230                 235                 240
Val Phe Ser Cys Ser Val Met His Glu Ala Leu His Asn His Tyr Thr
                245                 250                 255
Gln Lys Ser Leu Ser Leu Ser Pro Gly Lys
            260                 265

<210> SEQ ID NO 9
<211> LENGTH: 188
<212> TYPE: PRT
<213> ORGANISM: Homo Sapien

<400> SEQUENCE: 9

Met Asp Cys Arg Lys Met Ala Arg Phe Ser Tyr Ser Val Ile Trp Ile
1               5                   10                  15
Met Ala Ile Ser Lys Val Phe Glu Leu Gly Leu Val Ala Gly Leu Gly
            20                  25                  30
```

```
His Gln Glu Phe Ala Arg Pro Ser Arg Gly Tyr Leu Ala Phe Arg Asp
         35                  40                  45

Asp Ser Ile Trp Pro Gln Glu Pro Ala Ile Arg Pro Arg Ser Ser
 50                  55                  60

Gln Arg Val Pro Pro Met Gly Ile Gln His Ser Lys Glu Leu Asn Arg
 65                  70                  75                  80

Thr Cys Cys Leu Asn Gly Gly Ala Cys Met Leu Gly Ser Phe Cys Ala
                 85                  90                  95

Cys Pro Pro Ser Phe Tyr Gly Arg Asn Cys Glu His Asp Val Arg Lys
                100                 105                 110

Glu Asn Cys Gly Ser Val Pro His Asp Thr Trp Leu Pro Lys Lys Cys
            115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
                180                 185

<210> SEQ ID NO 10
<211> LENGTH: 139
<212> TYPE: PRT
<213> ORGANISM: Homo Sapien

<400> SEQUENCE: 10

Leu Gly His Gln Glu Phe Ala Arg Pro Ser Arg Gly Tyr Leu Ala Phe
 1               5                  10                  15

Arg Asp Asp Ser Ile Trp Pro Gln Glu Pro Ala Ile Arg Pro Arg
            20                  25                  30

Ser Ser Gln Arg Val Pro Pro Met Gly Ile Gln His Ser Lys Glu Leu
         35                  40                  45

Asn Arg Thr Cys Cys Leu Asn Gly Gly Ala Cys Met Leu Gly Ser Phe
 50                  55                  60

Cys Ala Cys Pro Pro Ser Phe Tyr Gly Arg Asn Cys Glu His Asp Val
 65                  70                  75                  80

Arg Lys Glu Asn Cys Gly Ser Val Pro His Asp Thr Trp Leu Pro Lys
                 85                  90                  95

Lys Cys Ser Leu Cys Lys Cys Trp His Gly Gln Leu Arg Cys Phe Pro
                100                 105                 110

Gln Ala Phe Leu Pro Gly Cys Asp Gly Leu Val Met Asp Glu His Leu
            115                 120                 125

Val Ala Ser Arg Thr Pro Glu Leu Pro Pro Ser
    130                 135

<210> SEQ ID NO 11
<211> LENGTH: 129
<212> TYPE: PRT
<213> ORGANISM: Homo Sapien

<400> SEQUENCE: 11

Arg Gly Tyr Leu Ala Phe Arg Asp Asp Ser Ile Trp Pro Gln Glu Glu
 1               5                  10                  15

Pro Ala Ile Arg Pro Arg Ser Ser Gln Arg Val Pro Pro Met Gly Ile
            20                  25                  30
```

```
Gln His Ser Lys Glu Leu Asn Arg Thr Cys Cys Leu Asn Gly Gly Ala
            35                  40                  45

Cys Met Leu Gly Ser Phe Cys Ala Cys Pro Pro Ser Phe Tyr Gly Arg
    50                  55                  60

Asn Cys Glu His Asp Val Arg Lys Glu Asn Cys Gly Ser Val Pro His
65                  70                  75                  80

Asp Thr Trp Leu Pro Lys Lys Cys Ser Leu Cys Lys Cys Trp His Gly
                85                  90                  95

Gln Leu Arg Cys Phe Pro Gln Ala Phe Leu Pro Gly Cys Asp Gly Leu
            100                 105                 110

Val Met Asp Glu His Leu Val Ala Ser Arg Thr Pro Glu Leu Pro Pro
            115                 120                 125

Ser

<210> SEQ ID NO 12
<211> LENGTH: 38
<212> TYPE: PRT
<213> ORGANISM: Homo Sapien

<400> SEQUENCE: 12

Ser Lys Glu Leu Asn Arg Thr Cys Cys Leu Asn Gly Gly Ala Cys Met
1               5                   10                  15

Leu Gly Ser Phe Cys Ala Cys Pro Pro Ser Phe Tyr Gly Arg Asn Cys
                20                  25                  30

Glu His Asp Val Arg Lys
            35

<210> SEQ ID NO 13
<211> LENGTH: 367
<212> TYPE: PRT
<213> ORGANISM: Homo Sapien

<400> SEQUENCE: 13

Leu Gly His Gln Glu Phe Ala Arg Pro Ser Arg Gly Tyr Leu Ala Phe
1               5                   10                  15

Arg Asp Asp Ser Ile Trp Pro Gln Glu Pro Ala Ile Arg Pro Arg
                20                  25                  30

Ser Ser Gln Arg Val Pro Pro Met Gly Ile Gln His Ser Lys Glu Leu
            35                  40                  45

Asn Arg Thr Cys Cys Leu Asn Gly Gly Ala Cys Met Leu Gly Ser Phe
50                  55                  60

Cys Ala Cys Pro Pro Ser Phe Tyr Gly Arg Asn Cys Glu His Asp Val
65                  70                  75                  80

Arg Lys Glu Asn Cys Gly Ser Val Pro His Asp Thr Trp Leu Pro Lys
                85                  90                  95

Lys Cys Ser Leu Cys Lys Cys Trp His Gly Gln Leu Arg Cys Phe Pro
            100                 105                 110

Gln Ala Phe Leu Pro Gly Cys Asp Gly Leu Val Met Asp Glu His Leu
            115                 120                 125

Val Ala Ser Arg Thr Pro Glu Leu Pro Pro Ser Val Asp Lys Thr His
            130                 135                 140

Thr Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175
```

```
Pro Glu Val Thr Cys Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
    210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Ser Arg Asp Glu Leu Thr Lys Asn Gln Val Ser Leu Thr Cys Leu
            275                 280                 285

Val Lys Gly Phe Tyr Pro Ser Asp Ile Ala Val Glu Trp Glu Ser Asn
        290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
            355                 360                 365

<210> SEQ ID NO 14
<211> LENGTH: 360
<212> TYPE: PRT
<213> ORGANISM: Homo Sapien

<400> SEQUENCE: 14

Arg Pro Ser Arg Gly Tyr Leu Ala Phe Arg Asp Asp Ser Ile Trp Pro
 1               5                  10                  15

Gln Glu Glu Pro Ala Ile Arg Pro Arg Ser Ser Gln Arg Val Pro Pro
             20                  25                  30

Met Gly Ile Gln His Ser Lys Glu Leu Asn Arg Thr Cys Cys Leu Asn
         35                  40                  45

Gly Gly Ala Cys Met Leu Gly Ser Phe Cys Ala Cys Pro Pro Ser Phe
     50                  55                  60

Tyr Gly Arg Asn Cys Glu His Asp Val Arg Lys Glu Asn Cys Gly Ser
65                  70                  75                  80

Val Pro His Asp Thr Trp Leu Pro Lys Lys Cys Ser Leu Cys Lys Cys
                 85                  90                  95

Trp His Gly Gln Leu Arg Cys Phe Pro Gln Ala Phe Leu Pro Gly Cys
            100                 105                 110

Asp Gly Leu Val Met Asp Glu His Leu Val Ala Ser Arg Thr Pro Glu
        115                 120                 125

Leu Pro Pro Ser Val Asp Lys Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190
```

Asp Gly Val Glu Val His Asn Ala Lys Thr Lys Pro Arg Glu Glu Gln
            195                 200                 205

Tyr Asn Ser Thr Tyr Arg Val Val Ser Val Leu Thr Val Leu His Gln
            210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
            290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
            355                 360

<210> SEQ ID NO 15
<211> LENGTH: 266
<212> TYPE: PRT
<213> ORGANISM: Homo Sapien

<400> SEQUENCE: 15

Ser Lys Glu Leu Asn Arg Thr Cys Cys Leu Asn Gly Gly Ala Cys Met
1               5                   10                  15

Leu Gly Ser Phe Cys Ala Cys Pro Pro Ser Phe Tyr Gly Arg Asn Cys
            20                  25                  30

Glu His Asp Val Arg Lys Val Asp Lys Thr His Thr Cys Pro Pro Cys
        35                  40                  45

Pro Ala Pro Glu Leu Leu Gly Gly Pro Ser Val Phe Leu Phe Pro Pro
    50                  55                  60

Lys Pro Lys Asp Thr Leu Met Ile Ser Arg Thr Pro Glu Val Thr Cys
65                  70                  75                  80

Val Val Val Asp Val Ser His Glu Asp Pro Glu Val Lys Phe Asn Trp
                85                  90                  95

Tyr Val Asp Gly Val Glu Val His Asn Ala Lys Thr Lys Pro Arg Glu
            100                 105                 110

Glu Gln Tyr Asn Ser Thr Tyr Arg Val Val Ser Val Leu Thr Val Leu
        115                 120                 125

His Gln Asp Trp Leu Asn Gly Lys Glu Tyr Lys Cys Lys Val Ser Asn
    130                 135                 140

Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Asp Glu
                165                 170                 175

Leu Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn

```
                           195                 200                 205
Asn Tyr Lys Thr Thr Pro Pro Val Leu Asp Ser Asp Gly Ser Phe Phe
    210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Pro Gly Lys
            260                 265

<210> SEQ ID NO 16
<211> LENGTH: 139
<212> TYPE: PRT
<213> ORGANISM: Homo Sapien

<400> SEQUENCE: 16

Leu Gly His Gln Glu Phe Ala Arg Pro Ser Arg Gly Asp Leu Ala Phe
1               5                   10                  15

Arg Asp Asp Ser Ile Trp Pro Gln Glu Glu Pro Ala Ile Arg Pro Arg
            20                  25                  30

Ser Ser Gln Arg Val Leu Pro Met Gly Ile Gln His Ser Lys Glu Leu
        35                  40                  45

Asn Arg Thr Cys Cys Leu Asn Gly Gly Thr Cys Met Leu Glu Ser Phe
    50                  55                  60

Cys Ala Cys Pro Pro Ser Phe Tyr Gly Arg Asn Cys Glu His Asp Val
65                  70                  75                  80

Arg Lys Glu Asn Cys Gly Ser Val Pro His Asp Thr Trp Leu Pro Lys
                85                  90                  95

Lys Cys Ser Leu Cys Lys Cys Trp His Gly Gln Leu Arg Cys Phe Pro
            100                 105                 110

Gln Ala Phe Leu Pro Gly Cys Asp Gly Leu Val Met Asp Glu His Leu
        115                 120                 125

Val Ala Ser Arg Thr Pro Glu Leu Pro Pro Ser
    130                 135

<210> SEQ ID NO 17
<211> LENGTH: 129
<212> TYPE: PRT
<213> ORGANISM: Homo Sapien

<400> SEQUENCE: 17

Arg Gly Asp Leu Ala Phe Arg Asp Asp Ser Ile Trp Pro Gln Glu Glu
1               5                   10                  15

Pro Ala Ile Arg Pro Arg Ser Ser Gln Arg Val Leu Pro Met Gly Ile
            20                  25                  30

Gln His Ser Lys Glu Leu Asn Arg Thr Cys Cys Leu Asn Gly Gly Thr
        35                  40                  45

Cys Met Leu Glu Ser Phe Cys Ala Cys Pro Pro Ser Phe Tyr Gly Arg
    50                  55                  60

Asn Cys Glu His Asp Val Arg Lys Glu Asn Cys Gly Ser Val Pro His
65                  70                  75                  80

Asp Thr Trp Leu Pro Lys Lys Cys Ser Leu Cys Lys Cys Trp His Gly
                85                  90                  95

Gln Leu Arg Cys Phe Pro Gln Ala Phe Leu Pro Gly Cys Asp Gly Leu
            100                 105                 110

Val Met Asp Glu His Leu Val Ala Ser Arg Thr Pro Glu Leu Pro Pro
```

```
              115                 120                 125

Ser

<210> SEQ ID NO 18
<211> LENGTH: 38
<212> TYPE: PRT
<213> ORGANISM: Homo Sapien

<400> SEQUENCE: 18

Ser Lys Glu Leu Asn Arg Thr Cys Cys Leu Asn Gly Gly Thr Cys Met
 1               5                  10                  15

Leu Glu Ser Phe Cys Ala Cys Pro Pro Ser Phe Tyr Gly Arg Asn Cys
             20                  25                  30

Glu His Asp Val Arg Lys
         35

<210> SEQ ID NO 19
<211> LENGTH: 367
<212> TYPE: PRT
<213> ORGANISM: Homo Sapien

<400> SEQUENCE: 19

Leu Gly His Gln Glu Phe Ala Arg Pro Ser Arg Gly Asp Leu Ala Phe
 1               5                  10                  15

Arg Asp Asp Ser Ile Trp Pro Gln Glu Pro Ala Ile Arg Pro Arg
             20                  25                  30

Ser Ser Gln Arg Val Leu Pro Met Gly Ile Gln His Ser Lys Glu Leu
             35                  40                  45

Asn Arg Thr Cys Cys Leu Asn Gly Gly Thr Cys Met Leu Glu Ser Phe
 50                  55                  60

Cys Ala Cys Pro Pro Ser Phe Tyr Gly Arg Asn Cys Glu His Asp Val
 65                  70                  75                  80

Arg Lys Glu Asn Cys Gly Ser Val Pro His Asp Thr Trp Leu Pro Lys
                 85                  90                  95

Lys Cys Ser Leu Cys Lys Cys Trp His Gly Gln Leu Arg Cys Phe Pro
            100                 105                 110

Gln Ala Phe Leu Pro Gly Cys Asp Gly Leu Val Met Asp Glu His Leu
            115                 120                 125

Val Ala Ser Arg Thr Pro Glu Leu Pro Pro Ser Val Asp Lys Thr His
        130                 135                 140

Thr Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
    210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270
```

```
Pro Ser Arg Asp Glu Leu Thr Lys Asn Gln Val Ser Leu Thr Cys Leu
            275                 280                 285

Val Lys Gly Phe Tyr Pro Ser Asp Ile Ala Val Glu Trp Glu Ser Asn
        290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
        355                 360                 365

<210> SEQ ID NO 20
<211> LENGTH: 360
<212> TYPE: PRT
<213> ORGANISM: Homo Sapien

<400> SEQUENCE: 20

Arg Pro Ser Arg Gly Asp Leu Ala Phe Arg Asp Asp Ser Ile Trp Pro
1               5                   10                  15

Gln Glu Glu Pro Ala Ile Arg Pro Arg Ser Ser Gln Arg Val Leu Pro
            20                  25                  30

Met Gly Ile Gln His Ser Lys Glu Leu Asn Arg Thr Cys Cys Leu Asn
        35                  40                  45

Gly Gly Thr Cys Met Leu Glu Ser Phe Cys Ala Cys Pro Pro Ser Phe
    50                  55                  60

Tyr Gly Arg Asn Cys Glu His Asp Val Arg Lys Glu Asn Cys Gly Ser
65                  70                  75                  80

Val Pro His Asp Thr Trp Leu Pro Lys Lys Cys Ser Leu Cys Lys Cys
                85                  90                  95

Trp His Gly Gln Leu Arg Cys Phe Pro Gln Ala Phe Leu Pro Gly Cys
            100                 105                 110

Asp Gly Leu Val Met Asp Glu His Leu Val Ala Ser Arg Thr Pro Glu
        115                 120                 125

Leu Pro Pro Ser Val Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
```

```
                275                 280                 285
Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
                340                 345                 350

Ser Leu Ser Leu Ser Pro Gly Lys
                355                 360

<210> SEQ ID NO 21
<211> LENGTH: 266
<212> TYPE: PRT
<213> ORGANISM: Homo Sapien

<400> SEQUENCE: 21

Ser Lys Glu Leu Asn Arg Thr Cys Cys Leu Asn Gly Gly Thr Cys Met
1               5                   10                  15

Leu Glu Ser Phe Cys Ala Cys Pro Pro Ser Phe Tyr Gly Arg Asn Cys
                20                  25                  30

Glu His Asp Val Arg Lys Val Asp Lys Thr His Thr Cys Pro Pro Cys
            35                  40                  45

Pro Ala Pro Glu Leu Leu Gly Gly Pro Ser Val Phe Leu Phe Pro Pro
    50                  55                  60

Lys Pro Lys Asp Thr Leu Met Ile Ser Arg Thr Pro Glu Val Thr Cys
65                  70                  75                  80

Val Val Val Asp Val Ser His Glu Asp Pro Glu Val Lys Phe Asn Trp
                85                  90                  95

Tyr Val Asp Gly Val Glu Val His Asn Ala Lys Thr Lys Pro Arg Glu
            100                 105                 110

Glu Gln Tyr Asn Ser Thr Tyr Arg Val Val Ser Val Leu Thr Val Leu
        115                 120                 125

His Gln Asp Trp Leu Asn Gly Lys Glu Tyr Lys Cys Lys Val Ser Asn
    130                 135                 140

Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Asp Glu
                165                 170                 175

Leu Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
        195                 200                 205

Asn Tyr Lys Thr Thr Pro Pro Val Leu Asp Ser Asp Gly Ser Phe Phe
    210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Pro Gly Lys
            260                 265

<210> SEQ ID NO 22
<211> LENGTH: 188
```

```
<212> TYPE: PRT
<213> ORGANISM: Homo Sapien

<400> SEQUENCE: 22

Met Asp Cys Arg Lys Met Val Arg Phe Ser Tyr Ser Val Ile Trp Ile
1               5                   10                  15

Met Ala Ile Ser Lys Ala Phe Glu Leu Gly Leu Val Ala Gly Leu Gly
                20                  25                  30

His Gln Glu Phe Ala Arg Pro Ser Arg Gly Asp Leu Ala Phe Arg Asp
            35                  40                  45

Asp Ser Ile Trp Pro Gln Glu Pro Ala Ile Arg Pro Arg Ser Ser
    50                  55                      60

Gln Arg Val Leu Pro Met Gly Ile Gln His Ser Lys Glu Leu Asn Arg
65                  70                  75                  80

Thr Cys Cys Leu Asn Gly Gly Ala Cys Met Leu Glu Ser Phe Cys Ala
                85                  90                  95

Cys Pro Pro Ser Phe Tyr Gly Arg Asn Cys Glu His Asp Val Arg Lys
                100                 105                 110

Glu Asn Cys Gly Ser Val Pro His Asp Thr Trp Leu Pro Lys Lys Cys
                115                 120                 125

Ser Leu Cys Lys Cys Trp His Gly Gln Leu Arg Cys Phe Pro Gln Ala
            130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Ala Gly Ile Cys Leu Ser Ile Gln Ser Tyr Tyr
                180                 185

<210> SEQ ID NO 23
<211> LENGTH: 139
<212> TYPE: PRT
<213> ORGANISM: Homo Sapien

<400> SEQUENCE: 23

Leu Gly His Gln Glu Phe Ala Arg Pro Ser Arg Gly Asp Leu Ala Phe
1               5                   10                  15

Arg Asp Asp Ser Ile Trp Pro Gln Glu Pro Ala Ile Arg Pro Arg
                20                  25                      30

Ser Ser Gln Arg Val Leu Pro Met Gly Ile Gln His Ser Lys Glu Leu
            35                  40                  45

Asn Arg Thr Cys Cys Leu Asn Gly Gly Thr Cys Met Leu Glu Ser Phe
    50                  55                      60

Cys Ala Cys Pro Pro Ser Phe Tyr Gly Arg Asn Cys Glu His Asp Val
65                  70                  75                  80

Arg Lys Glu Asn Cys Gly Ser Val Pro His Asp Thr Trp Leu Pro Lys
                85                  90                  95

Lys Cys Ser Leu Cys Lys Cys Trp His Gly Gln Leu Arg Cys Phe Pro
                100                 105                 110

Gln Ala Phe Leu Pro Gly Cys Asp Gly Leu Val Met Asp Glu His Leu
            115                 120                 125

Val Ala Ser Arg Thr Pro Glu Leu Pro Pro Ser
        130                 135

<210> SEQ ID NO 24
<211> LENGTH: 129
```

<212> TYPE: PRT
<213> ORGANISM: Homo Sapien

<400> SEQUENCE: 24

Arg Gly Asp Leu Ala Phe Arg Asp Asp Ser Ile Trp Pro Gln Glu Glu
 1               5                  10                  15

Pro Ala Ile Arg Pro Arg Ser Ser Gln Arg Val Leu Pro Met Gly Ile
            20                  25                  30

Gln His Ser Lys Glu Leu Asn Arg Thr Cys Cys Leu Asn Gly Gly Ala
        35                  40                  45

Cys Met Leu Glu Ser Phe Cys Ala Cys Pro Pro Ser Phe Tyr Gly Arg
    50                  55                  60

Asn Cys Glu His Asp Val Arg Lys Glu Asn Cys Gly Ser Val Pro His
65                  70                  75                  80

Asp Thr Trp Leu Pro Lys Lys Cys Ser Leu Cys Lys Cys Trp His Gly
                85                  90                  95

Gln Leu Arg Cys Phe Pro Gln Ala Phe Leu Pro Gly Cys Asp Gly Leu
            100                 105                 110

Val Met Asp Glu His Leu Val Ala Ser Arg Thr Pro Glu Leu Pro Pro
        115                 120                 125

Ser

<210> SEQ ID NO 25
<211> LENGTH: 38
<212> TYPE: PRT
<213> ORGANISM: Homo Sapien

<400> SEQUENCE: 25

Ser Lys Glu Leu Asn Arg Thr Cys Cys Leu Asn Gly Gly Ala Cys Met
 1               5                  10                  15

Leu Glu Ser Phe Cys Ala Cys Pro Pro Ser Phe Tyr Gly Arg Asn Cys
            20                  25                  30

Glu His Asp Val Arg Lys
        35

<210> SEQ ID NO 26
<211> LENGTH: 367
<212> TYPE: PRT
<213> ORGANISM: Homo Sapien

<400> SEQUENCE: 26

Leu Gly His Gln Glu Phe Ala Arg Pro Ser Arg Gly Asp Leu Ala Phe
 1               5                  10                  15

Arg Asp Asp Ser Ile Trp Pro Gln Glu Glu Pro Ala Ile Arg Pro Arg
            20                  25                  30

Ser Ser Gln Arg Val Leu Pro Met Gly Ile Gln His Ser Lys Glu Leu
        35                  40                  45

Asn Arg Thr Cys Cys Leu Asn Gly Gly Ala Cys Met Leu Glu Ser Phe
    50                  55                  60

Cys Ala Cys Pro Pro Ser Phe Tyr Gly Arg Asn Cys Glu His Asp Val
65                  70                  75                  80

Arg Lys Glu Asn Cys Gly Ser Val Pro His Asp Thr Trp Leu Pro Lys
                85                  90                  95

Lys Cys Ser Leu Cys Lys Cys Trp His Gly Gln Leu Arg Cys Phe Pro
            100                 105                 110

Gln Ala Phe Leu Pro Gly Cys Asp Gly Leu Val Met Asp Glu His Leu
        115                 120                 125

```
Val Ala Ser Arg Thr Pro Glu Leu Pro Pro Ser Val Asp Lys Thr His
    130                 135                 140

Thr Cys Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
    210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Ser Arg Asp Glu Leu Thr Lys Asn Gln Val Ser Leu Thr Cys Leu
        275                 280                 285

Val Lys Gly Phe Tyr Pro Ser Asp Ile Ala Val Glu Trp Glu Ser Asn
    290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
        355                 360                 365

<210> SEQ ID NO 27
<211> LENGTH: 360
<212> TYPE: PRT
<213> ORGANISM: Homo Sapien

<400> SEQUENCE: 27

Arg Pro Ser Arg Gly Asp Leu Ala Phe Arg Asp Asp Ser Ile Trp Pro
1               5                   10                  15

Gln Glu Glu Pro Ala Ile Arg Pro Arg Ser Ser Gln Arg Val Leu Pro
            20                  25                  30

Met Gly Ile Gln His Ser Lys Glu Leu Asn Arg Thr Cys Cys Leu Asn
        35                  40                  45

Gly Gly Ala Cys Met Leu Glu Ser Phe Cys Ala Cys Pro Ser Phe
    50                  55                  60

Tyr Gly Arg Asn Cys Glu His Asp Val Arg Lys Glu Asn Cys Gly Ser
65                  70                  75                  80

Val Pro His Asp Thr Trp Leu Pro Lys Lys Cys Ser Leu Cys Lys Cys
                85                  90                  95

Trp His Gly Gln Leu Arg Cys Phe Pro Gln Ala Phe Leu Pro Gly Cys
            100                 105                 110

Asp Gly Leu Val Met Asp Glu His Leu Val Ala Ser Arg Thr Pro Glu
        115                 120                 125

Leu Pro Pro Ser Val Asp Lys Thr His Thr Cys Pro Cys Pro Ala
```

```
              130                 135                 140
Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 28
<211> LENGTH: 266
<212> TYPE: PRT
<213> ORGANISM: Homo Sapien

<400> SEQUENCE: 28

Ser Lys Glu Leu Asn Arg Thr Cys Cys Leu Asn Gly Gly Ala Cys Met
  1               5                  10                  15

Leu Glu Ser Phe Cys Ala Cys Pro Pro Ser Phe Tyr Gly Arg Asn Cys
                 20                  25                  30

Glu His Asp Val Arg Lys Val Asp Lys Thr His Thr Cys Pro Pro Cys
             35                  40                  45

Pro Ala Pro Glu Leu Leu Gly Gly Pro Ser Val Phe Leu Phe Pro Pro
         50                  55                  60

Lys Pro Lys Asp Thr Leu Met Ile Ser Arg Thr Pro Glu Val Thr Cys
 65                  70                  75                  80

Val Val Val Asp Val Ser His Glu Asp Pro Glu Val Lys Phe Asn Trp
                 85                  90                  95

Tyr Val Asp Gly Val Glu Val His Asn Ala Lys Thr Lys Pro Arg Glu
            100                 105                 110

Glu Gln Tyr Asn Ser Thr Tyr Arg Val Val Ser Val Leu Thr Val Leu
        115                 120                 125

His Gln Asp Trp Leu Asn Gly Lys Glu Tyr Lys Cys Lys Val Ser Asn
    130                 135                 140
```

```
Lys Ala Leu Pro Ala Pro Ile Glu Lys Thr Ile Ser Lys Ala Lys Gly
145                 150                 155                 160

Gln Pro Arg Glu Pro Gln Val Tyr Thr Leu Pro Pro Ser Arg Asp Glu
            165                 170                 175

Leu Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
            195                 200                 205

Asn Tyr Lys Thr Thr Pro Pro Val Leu Asp Ser Asp Gly Ser Phe Phe
        210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Pro Gly Lys
            260                 265
```

<210> SEQ ID NO 29
<211> LENGTH: 50
<212> TYPE: DNA
<213> ORGANISM: Homo Sapien

<400> SEQUENCE: 29
ctgttgaagc ttgcggccgc ttcaatatgg actgcaggaa gatgggatgg          50

<210> SEQ ID NO 30
<211> LENGTH: 43
<212> TYPE: DNA
<213> ORGANISM: Homo Sapien

<400> SEQUENCE: 30
gatattctcg aggcggccgc ttaagacggt ggtagttctg gag                 43

<210> SEQ ID NO 31
<211> LENGTH: 45
<212> TYPE: DNA
<213> ORGANISM: Homo Sapien

<400> SEQUENCE: 31
gatattctcg aggcggccgc ttaatagtag ctttgtatag aaagg               45

<210> SEQ ID NO 32
<211> LENGTH: 44
<212> TYPE: DNA
<213> ORGANISM: Homo Sapien

<400> SEQUENCE: 32
gcctcagcgg ccgcgtcgac cactggcttc aggagctgaa tacc                44

<210> SEQ ID NO 33
<211> LENGTH: 27
<212> TYPE: DNA
<213> ORGANISM: Homo Sapien

<400> SEQUENCE: 33
agagcgggcg gccgcactca tttcccg                                   27

<210> SEQ ID NO 34
<211> LENGTH: 44
<212> TYPE: DNA
<213> ORGANISM: Homo Sapien

<400> SEQUENCE: 34

```
gcctgaatgg gggagcctgc atgctgggat cctttgtgc ctgc                        44
```

<210> SEQ ID NO 35
<211> LENGTH: 42
<212> TYPE: DNA
<213> ORGANISM: Homo Sapien

<400> SEQUENCE: 35

```
gcaggcacaa aaggatccca gcatgcaggc tcccccattc ag                         42
```

<210> SEQ ID NO 36
<211> LENGTH: 593
<212> TYPE: DNA
<213> ORGANISM: Homo Sapien

<400> SEQUENCE: 36

```
ggatccttca atatggactg caggaagatg gcccgcttct cttacagtgt gatttggatc      60
atggccattt ctaaagtctt tgaactggga ttagttgccg ggctgggcca tcaggaattt     120
gctcgtccat ctcggggata cctggccttc agagatgaca gcatttggcc ccaggaggag     180
cctgcaattc ggcctcggtc tttcccagcgt gtgccgccca tggggataca gcacagtaag    240
gagctaaaca gaacctgctg cctgaatggg ggaacctgca tgctggggtc cttttgtgcc     300
tgccctccct ccttctacgg acggaactgt gagcacgatg tgcgcaaaga gaactgtggg     360
tctgtgcccc atgacacctg gctgcccaag aagtgttccc tgtgtaaatg ctggcacggt     420
cagctccgct gctttcctca ggcatttcta cccggctgtg atggccttgt gatggatgag     480
cacctcgtgg cttccaggac tccagaacta ccaccgtctg cacgtactac cactttatg     540
ctagttggca tctgcctttc tatacaaagc tactattaag cggccgcctc gag            593
```

<210> SEQ ID NO 37
<211> LENGTH: 567
<212> TYPE: DNA
<213> ORGANISM: Homo Sapien

<400> SEQUENCE: 37

```
atggactgca ggaagatggt ccgcttctct tacagtgtga tttggatcat ggccatttct      60
aaagcctttg aactgggatt agttgccggg ctgggccatc aggaatttgc tcgtccatct     120
cggggagacc tggccttcag agatgacagc atttggcccc aggaggagcc tgcaattcgg     180
cctcggtctt cccagcgtgt gctgcccatg gaatacagc acagtaagga ctaaacaga      240
acctgctgcc tgaatggggg aacctgcatg ctggagtcct tttgtgcctg ccctccctcc     300
ttctacggac ggaactgtga gcacgatgtg cgcaaagaga actgtgggtc tgtgccccat     360
gacacctggc tgcccaagaa gtgttccctg tgtaaatgct ggcacggtca gctccgctgc     420
tttcctcagg catttctacc cggctgtgat ggccttgtga tggatgagca cctcgtggct     480
tccaggactc cagaactacc accgtctgca cgtactacca cttttatgct agctggcatc     540
tgcctttcta tacaaagcta ctattaa                                         567
```